(12) United States Patent
Yanagihara et al.

(10) Patent No.: US 9,670,514 B2
(45) Date of Patent: Jun. 6, 2017

(54) METHOD FOR PRODUCING POLYSACCHARIDE

(75) Inventors: Fusamitsu Yanagihara, Kyoto (JP); Kentaro Matsuo, Kyoto (JP); Miki Kusano, Kyoto (JP)

(73) Assignee: SANYO CHEMICAL INDUSTRIES, LTD., Kyoto (JP)

( * ) Notice: Subject to any disclaimer, the term of this patent is extended or adjusted under 35 U.S.C. 154(b) by 4 days.

(21) Appl. No.: 14/123,291

(22) PCT Filed: May 31, 2012

(86) PCT No.: PCT/JP2012/064241
§ 371 (c)(1),
(2), (4) Date: Jan. 29, 2014

(87) PCT Pub. No.: WO2012/169437
PCT Pub. Date: Dec. 13, 2012

(65) Prior Publication Data
US 2014/0134679 A1    May 15, 2014

(30) Foreign Application Priority Data

Jun. 9, 2011 (JP) ................. 2011-128778
Jul. 19, 2011 (JP) ................. 2011-158077
Sep. 7, 2011 (JP) ................. 2011-195239
Sep. 12, 2011 (JP) ................. 2011-197796

(51) Int. Cl.
*C12P 19/04* (2006.01)
*C12P 19/26* (2006.01)

(52) U.S. Cl.
CPC ............... *C12P 19/04* (2013.01); *C12P 19/26* (2013.01)

(58) Field of Classification Search
None
See application file for complete search history.

(56) References Cited

U.S. PATENT DOCUMENTS

| | | | |
|---|---|---|---|
| 4,141,973 A | 2/1979 | Balazs | |
| 4,303,676 A | 12/1981 | Balazs | |
| 2002/0068331 A1* | 6/2002 | Wong et al. | 435/74 |

FOREIGN PATENT DOCUMENTS

| | | |
|---|---|---|
| JP | 58-56692 | 4/1983 |
| JP | 02-231093 | 9/1990 |
| JP | 07-079792 | 3/1995 |
| JP | 2000-4886 | 1/2000 |
| JP | 2005-160321 | 6/2005 |
| JP | 2007-330112 | 12/2007 |
| JP | 2009-536031 | 10/2009 |
| WO | 86-04355 | 7/1986 |
| WO | 2007/130638 | 11/2007 |

OTHER PUBLICATIONS

Tlapak-Simmons et al. Biochemistry (2004) 43, 9234-9242.*
Trombetta et al. The Embo J. (1999) 18 (12) 3282-3292.*
Postel, E. H. The Intern. J. Biochem. Cell Biol. (1998) 1291-1295.*
Chong et al., "Microbial Hyaluronic acid production", Appl Microbiol Biotechnol, vol. 66, Nov. 13, 2004, pp. 341-351.
Tlapak-Simmons et al., "Kinetic Characterization of the Recombinant Hyaluronan Synthases from *Streptococcus pyogenes* and *Streptococcus equisimilis*", The Journal of Biological Chemistry, vol. 274, No. 7, Feb. 12, 1999, pp. 4246-4253.
International Search Report issued Aug. 14, 2012 in International (PCT) Application No. PCT/JP2012/064241.
English translation of Written Opinion of the International Searching Authority issued Aug. 14, 2012 in International (PCT) Application No. PCT/JP2012/064241.
Itano et al., "Hyaluronan Synthase: Functional Analysis of Hyaluronan by Gene Modification", Protein, Nucleic Acid and Enzyme, vol. 43, 1998, pp. 2387-2393, concise explanation of relevance in Written Opinion (CB).
DeAngelis et al., "Identification and Molecular Cloning of a Unique Hyaluronan Synthase from *Pasteurella multocida*", The Journal of Biological Chemistry, vol. 273, No. 14, Apr. 1998, pp. 8454-8458.
De Luca et al., "Enzymatic Synthesis of Hyaluronic Acid with Regeneration of Sugar Nucleotides", J. Am. Chem. Soc., 1995, vol. 117, pp. 5869-5870.
Peter Prehm, "Synthesis of hyaluronate in differentiated teratocarcinoma cells", Biochem. J., 1983, vol. 211, pp. 191-198.

* cited by examiner

*Primary Examiner* — Suzanne M Noakes
(74) *Attorney, Agent, or Firm* — Wenderoth, Lind & Ponack, L.L.P.

(57) ABSTRACT

The present invention aims to provide a method for producing a polysaccharide with high efficiency using a polysaccharide synthase. The present invention provides a method for producing a polysaccharide, including allowing polysaccharide synthase (B) to act on ribonucleoside diphosphate-monosaccharide (A) to produce a polysaccharide, wherein in 10 to 100% of the duration in which (B) acts on (A), the concentration of ribonucleoside diphosphate in a reaction solution is lower than 100 times an inhibitory concentration $IC_{50}$ against polysaccharide synthase (B).

4 Claims, No Drawings

```
                        SEQUENCE LISTING

<160> NUMBER OF SEQ ID NOS: 13

<210> SEQ ID NO 1
<211> LENGTH: 419
<212> TYPE: PRT
<213> ORGANISM: STREPTOCOCCUS

<400> SEQUENCE: 1

Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
                20                  25                  30

Val Gly Ile Tyr Gly Val Ile Leu Ile Thr Tyr Leu Val Ile Lys Leu
            35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
                100                 105                 110

Ile Glu Glu Tyr Val Asn Arg Glu Val Asp Ile Cys Arg Asn Val Ile
            115                 120                 125

Val His Arg Ser Leu Val Asn Lys Gly Lys Arg His Ala Gln Ala Trp
        130                 135                 140

Ala Phe Glu Arg Ser Asp Ala Asp Val Phe Leu Thr Val Asp Ser Asp
145                 150                 155                 160

Thr Tyr Ile Tyr Pro Asn Ala Leu Glu Glu Leu Leu Lys Ser Phe Asn
                165                 170                 175
```

-continued

```
Asp Glu Thr Val Tyr Ala Ala Thr Gly His Leu Asn Ala Arg Asn Arg
            180                 185                 190

Gln Thr Asn Leu Leu Thr Arg Leu Thr Asp Ile Arg Tyr Asp Asn Ala
        195                 200                 205

Phe Gly Val Glu Arg Ala Ala Gln Ser Leu Thr Gly Asn Ile Leu Val
    210                 215                 220

Cys Ser Gly Pro Leu Ser Ile Tyr Arg Arg Glu Val Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 2
<211> LENGTH: 806
<212> TYPE: PRT
<213> ORGANISM: Vicia faba

<400> SEQUENCE: 2

Met Ala Thr Glu Arg Leu Thr Arg Val His Ser Leu Arg Glu Arg Leu
1               5                   10                  15

Asp Glu Thr Leu Thr Ala Asn Arg Asn Glu Ile Leu Ala Leu Leu Ser
            20                  25                  30

Arg Ile Glu Ala Lys Gly Lys Gly Ile Leu Gln His His Gln Val Ile
        35                  40                  45

Ala Glu Phe Glu Glu Ile Pro Glu Glu Asn Arg Gln Lys Leu Thr Asp
    50                  55                  60

Gly Ala Phe Gly Glu Val Leu Arg Ser Thr Gln Glu Ala Ile Val Leu
65                  70                  75                  80

Pro Pro Trp Val Ala Leu Ala Val Arg Pro Arg Pro Gly Val Trp Glu
                85                  90                  95

Tyr Leu Arg Val Asn Val His Ala Leu Val Val Glu Asn Leu Gln Pro
            100                 105                 110

Ala Glu Phe Leu Lys Phe Lys Glu Glu Leu Val Asp Gly Ser Ala Asn
        115                 120                 125
```

```
Gly Asn Phe Val Leu Glu Leu Asp Phe Glu Pro Phe Thr Ala Ser Phe
        130                 135                 140

Pro Arg Pro Thr Leu Asn Lys Ser Ile Gly Asn Gly Val Gln Phe Leu
145                 150                 155                 160

Asn Arg His Leu Ser Ala Lys Leu Phe His Asp Lys Glu Ser Leu His
                165                 170                 175

Pro Leu Glu Phe Leu Arg Leu His Ser Tyr Lys Gly Lys Thr Leu
                180                 185                 190

Met Leu Asn Asp Arg Ile Gln Asn Pro Asp Ser Leu Gln His Val Leu
        195                 200                 205

Arg Lys Ala Glu Glu Tyr Leu Ser Thr Val Asp Pro Glu Thr Pro Tyr
210                 215                 220

Ser Glu Phe Glu His Arg Phe Gln Glu Ile Gly Leu Glu Arg Gly Trp
225                 230                 235                 240

Gly Asp Ser Ala Glu Arg Val Leu Glu Ser Ile Gln Leu Leu Leu Asp
                245                 250                 255

Leu Leu Glu Ala Pro Asp Pro Cys Thr Leu Glu Thr Phe Leu Asp Arg
                260                 265                 270

Ile Pro Met Val Phe Asn Val Val Ile Leu Ser Pro His Gly Tyr Phe
        275                 280                 285

Ala Gln Asp Asp Val Leu Gly Tyr Pro Asp Thr Gly Gly Gln Val Val
        290                 295                 300

Tyr Ile Leu Asp Gln Val Arg Ala Leu Glu Ser Glu Met Leu Asn Arg
305                 310                 315                 320

Ile Lys Lys Gln Gly Leu Asp Ile Val Pro Arg Ile Leu Ile Ile Thr
                325                 330                 335

Arg Leu Leu Pro Asp Ala Val Gly Thr Thr Cys Gly Gln Arg Leu Glu
                340                 345                 350

Lys Val Tyr Gly Thr Glu His Cys His Ile Leu Arg Val Pro Phe Arg
        355                 360                 365

Asp Gln Lys Gly Ile Val Arg Lys Trp Ile Ser Arg Phe Glu Val Trp
        370                 375                 380

Pro Tyr Leu Glu Thr Tyr Thr Glu Asp Val Ala His Glu Leu Ala Lys
385                 390                 395                 400

Glu Leu Gln Gly Lys Pro Asp Leu Ile Val Gly Asn Tyr Ser Asp Gly
                405                 410                 415

Asn Ile Val Ala Ser Leu Leu Ala His Lys Leu Gly Val Thr Gln Cys
                420                 425                 430

Thr Ile Ala His Ala Leu Glu Lys Thr Lys Tyr Pro Glu Ser Asp Ile
        435                 440                 445

Tyr Trp Lys Lys Phe Glu Glu Lys Tyr His Phe Ser Cys Gln Phe Thr
450                 455                 460

Ala Asp Leu Phe Ala Met Asn His Thr Asp Phe Ile Ile Thr Ser Thr
465                 470                 475                 480

Phe Gln Glu Ile Ala Gly Ser Lys Asp Thr Val Gly Gln Tyr Glu Ser
                485                 490                 495

His Thr Ala Phe Thr Leu Pro Gly Leu Tyr Arg Val Val His Gly Ile
                500                 505                 510

Asp Val Phe Asp Pro Lys Phe Asn Ile Val Ser Pro Gly Ala Asp Gln
        515                 520                 525

Thr Ile Tyr Phe Pro Tyr Thr Glu Thr Ser Arg Arg Leu Thr Ser Phe
530                 535                 540
```

-continued

Tyr Pro Glu Ile Glu Glu Leu Leu Tyr Ser Thr Val Glu Asn Glu Glu
545                 550                 555                 560

His Ile Cys Val Leu Lys Asp Arg Ser Lys Pro Ile Ile Phe Thr Met
                565                 570                 575

Ala Arg Leu Asp Arg Val Lys Asn Ile Thr Gly Leu Val Glu Trp Tyr
            580                 585                 590

Gly Lys Asn Ala Lys Leu Arg Glu Leu Val Asn Leu Val Val Val Ala
        595                 600                 605

Gly Asp Arg Arg Lys Glu Ser Lys Asp Leu Glu Lys Ala Glu Met
    610                 615                 620

Lys Lys Met Tyr Glu Leu Ile Glu Thr Tyr Lys Leu Asn Gly Gln Phe
625                 630                 635                 640

Arg Trp Ile Ser Ser Gln Met Asn Arg Val Arg Asn Gly Glu Leu Tyr
                645                 650                 655

Arg Val Ile Cys Asp Thr Lys Gly Ala Phe Val Gln Pro Ala Val Tyr
            660                 665                 670

Glu Ala Phe Gly Leu Thr Val Val Glu Ala Met Ala Thr Gly Leu Pro
        675                 680                 685

Thr Phe Ala Thr Leu Asn Gly Gly Pro Ala Glu Ile Ile Val His Gly
690                 695                 700

Lys Ser Gly Phe His Ile Asp Pro Tyr His Gly Asp Arg Ala Ala Asp
705                 710                 715                 720

Leu Leu Val Glu Phe Phe Lys Val Lys Ala Asp Pro Ser His Trp
                725                 730                 735

Asp Lys Ile Ser Leu Gly Gly Leu Gln Arg Ile Glu Glu Lys Tyr Thr
            740                 745                 750

Trp Gln Ile Tyr Ser Gln Arg Leu Leu Thr Leu Thr Gly Val Tyr Gly
        755                 760                 765

Phe Trp Lys His Val Ser Asn Leu Asp Arg Leu Glu Ser Arg Arg Tyr
770                 775                 780

Leu Glu Met Phe Tyr Ala Leu Lys Tyr Arg Lys Leu Ala Glu Ser Val
785                 790                 795                 800

Pro Leu Ala Val Glu Glu
            805

<210> SEQ ID NO 3
<211> LENGTH: 334
<212> TYPE: PRT
<213> ORGANISM: Corynebacterium glutamicum

<400> SEQUENCE: 3

Met Ala Ala Asp Ser Asp Leu Ser Val His Asp Ala Tyr Leu Lys Glu
1               5                   10                  15

His Val Ala Pro Val Lys Ala Ile Asn Trp Asn Ser Ile Pro Asp Ser
            20                  25                  30

Lys Asp Leu Glu Val Trp Asp Arg Leu Thr Gly Asn Phe Trp Leu Pro
        35                  40                  45

Glu Lys Val Pro Val Ser Asn Asp Ile Lys Ser Trp Gly Thr Leu Asn
    50                  55                  60

Glu Val Glu Lys Ala Ala Thr Met Arg Val Phe Thr Gly Leu Thr Leu
65                  70                  75                  80

Leu Asp Thr Ile Gln Gly Thr Val Gly Ala Ile Ser Leu Leu Pro Asp
                85                  90                  95

Ala Asp Ser Leu His Glu Glu Ala Val Leu Thr Asn Ile Ala Phe Met
            100                 105                 110

Glu Ser Val His Ala Lys Ser Tyr Ser Asn Ile Phe Met Thr Leu Ala
            115                 120                 125

Ser Thr Ala Glu Ile Asn Asp Ala Phe Arg Trp Ser Glu Glu Asn Glu
130                 135                 140

Asn Leu Gln Arg Lys Ala Lys Ile Ile Leu Ser Tyr Tyr Glu Gly Asp
145                 150                 155                 160

Asp Pro Leu Lys Arg Lys Ile Ala Ser Val Ile Leu Glu Ser Phe Leu
                165                 170                 175

Phe Tyr Ser Gly Phe Tyr Leu Pro Met Tyr Trp Ser Ser His Ser Lys
            180                 185                 190

Leu Thr Asn Thr Ala Asp Val Ile Arg Leu Ile Ile Arg Asp Glu Ala
        195                 200                 205

Val His Gly Tyr Tyr Ile Gly Tyr Lys Tyr Gln Lys Ala Val Ala Lys
    210                 215                 220

Glu Thr Pro Glu Arg Gln Glu Glu Leu Lys Glu Tyr Thr Phe Asp Leu
225                 230                 235                 240

Leu Tyr Asp Leu Tyr Asp Asn Glu Thr Gln Tyr Ser Glu Asp Leu Tyr
                245                 250                 255

Asp Asp Leu Gly Trp Thr Glu Asp Val Lys Arg Phe Leu Arg Tyr Ile
            260                 265                 270

Ala Asn Lys Ala Leu Asn Asn Leu Gly Tyr Glu Gly Leu Phe Pro Ala
        275                 280                 285

Asp Glu Thr Lys Val Ser Pro Asn Ile Leu Ser Ala Leu Ser Pro Asn
    290                 295                 300

Ala Asp Glu Asn His Asp Phe Phe Ser Gly Gly Ser Ser Tyr Val
305                 310                 315                 320

Ile Gly Lys Ala Glu Asn Thr Glu Asp Asp Asp Trp Asp Phe
                325                 330

<210> SEQ ID NO 4
<211> LENGTH: 470
<212> TYPE: PRT
<213> ORGANISM: Escherichia coli

<400> SEQUENCE: 4

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
            20                  25                  30

Leu Asn Phe Ser His Gly Asp Tyr Ala Glu His Gly Gln Arg Ile Gln
        35                  40                  45

Asn Leu Arg Asn Val Met Ser Lys Thr Gly Lys Thr Ala Ala Ile Leu
50                  55                  60

Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
            100                 105                 110

Phe Thr Thr Asp Leu Ser Val Gly Asn Thr Val Leu Val Asp Asp Gly
        115                 120                 125

Leu Ile Gly Met Glu Val Thr Ala Ile Glu Gly Asn Lys Val Ile Cys
    130                 135                 140

Lys Val Leu Asn Asn Gly Asp Leu Gly Glu Asn Lys Gly Val Asn Leu

```
                145                 150                 155                 160
Pro Gly Val Ser Ile Ala Leu Pro Ala Leu Ala Glu Lys Asp Lys Gln
                    165                 170                 175
Asp Leu Ile Phe Gly Cys Glu Gln Gly Val Asp Phe Val Ala Ala Ser
                180                 185                 190
Phe Ile Arg Lys Arg Ser Asp Val Glu Ile Arg Glu His Leu Lys
            195                 200                 205
Ala His Gly Gly Glu Asn Ile His Ile Ser Lys Ile Glu Asn Gln
        210                 215                 220
Glu Gly Leu Asn Asn Phe Asp Glu Ile Leu Glu Ala Ser Asp Gly Ile
225                 230                 235                 240
Met Val Ala Arg Gly Asp Leu Gly Val Glu Ile Pro Val Glu Glu Val
                245                 250                 255
Ile Phe Ala Gln Lys Met Met Ile Glu Lys Cys Ile Arg Ala Arg Lys
                260                 265                 270
Val Val Ile Thr Ala Thr Gln Met Leu Asp Ser Met Ile Lys Asn Pro
            275                 280                 285
Arg Pro Thr Arg Ala Glu Ala Gly Asp Val Ala Asn Ala Ile Leu Asp
    290                 295                 300
Gly Thr Asp Ala Val Met Leu Ser Gly Glu Ser Ala Lys Gly Lys Tyr
305                 310                 315                 320
Pro Leu Glu Ala Val Ser Ile Met Ala Thr Ile Cys Glu Arg Thr Asp
                325                 330                 335
Arg Val Met Asn Ser Arg Leu Glu Phe Asn Asn Asp Asn Arg Lys Leu
                340                 345                 350
Arg Ile Thr Glu Ala Val Cys Arg Gly Ala Val Glu Thr Ala Glu Lys
            355                 360                 365
Leu Asp Ala Pro Leu Ile Val Val Ala Thr Gln Gly Gly Lys Ser Ala
        370                 375                 380
Arg Ala Val Arg Lys Tyr Phe Pro Asp Ala Thr Ile Leu Ala Leu Thr
385                 390                 395                 400
Thr Asn Glu Lys Thr Ala His Gln Leu Val Leu Ser Lys Gly Val Val
                405                 410                 415
Pro Gln Leu Val Lys Glu Ile Thr Ser Thr Asp Asp Phe Tyr Arg Leu
                420                 425                 430
Gly Lys Glu Leu Ala Leu Gln Ser Gly Leu Ala His Lys Gly Asp Val
            435                 440                 445
Val Val Met Val Ser Gly Ala Leu Val Pro Ser Gly Thr Thr Asn Thr
        450                 455                 460
Ala Ser Val His Val Leu
465                 470

<210> SEQ ID NO 5
<211> LENGTH: 199
<212> TYPE: PRT
<213> ORGANISM: Escherichia coli

<400> SEQUENCE: 5

Met Lys Gln Ser His Phe Phe Ala His Leu Ser Arg Leu Lys Leu Ile
1               5                   10                  15
Asn Arg Trp Pro Leu Met Arg Asn Val Arg Thr Glu Asn Val Ser Glu
                20                  25                  30
His Ser Leu Gln Val Ala Met Val Ala His Ala Leu Ala Ala Ile Lys
            35                  40                  45
```

```
Asn Arg Lys Phe Gly Gly Asn Val Asn Ala Glu Arg Ile Ala Leu Leu
    50                  55                  60
Ala Met Tyr His Asp Ala Ser Glu Val Leu Thr Gly Asp Leu Pro Thr
65                  70                  75                  80
Pro Val Lys Tyr Phe Asn Ser Gln Ile Ala Gln Glu Tyr Lys Ala Ile
                85                  90                  95
Glu Lys Ile Ala Gln Gln Lys Leu Val Asp Met Val Pro Glu Glu Leu
            100                 105                 110
Arg Asp Ile Phe Ala Pro Leu Ile Asp Glu His Ala Tyr Ser Asp Glu
        115                 120                 125
Glu Lys Ser Leu Val Lys Gln Ala Asp Ala Leu Cys Ala Tyr Leu Lys
    130                 135                 140
Cys Leu Glu Glu Leu Ala Ala Gly Asn Asn Glu Phe Leu Leu Ala Lys
145                 150                 155                 160
Thr Arg Leu Glu Ala Thr Leu Glu Ala Arg Arg Ser Gln Glu Met Asp
                165                 170                 175
Tyr Phe Met Glu Ile Phe Val Pro Ser Phe His Leu Ser Leu Asp Glu
            180                 185                 190
Ile Ser Gln Asp Ser Pro Leu
        195

<210> SEQ ID NO 6
<211> LENGTH: 711
<212> TYPE: PRT
<213> ORGANISM: Escherichia coli

<400> SEQUENCE: 6

Met Leu Asn Pro Ile Val Arg Lys Phe Gln Tyr Gly Gln His Thr Val
1               5                   10                  15
Thr Leu Glu Thr Gly Met Met Ala Arg Gln Ala Thr Ala Ala Val Met
                20                  25                  30
Val Ser Met Asp Asp Thr Ala Val Phe Val Thr Val Val Gly Gln Lys
            35                  40                  45
Lys Ala Lys Pro Gly Gln Asp Phe Phe Pro Leu Thr Val Asn Tyr Gln
    50                  55                  60
Glu Arg Thr Tyr Ala Ala Gly Arg Ile Pro Gly Ser Phe Phe Arg Arg
65                  70                  75                  80
Glu Gly Arg Pro Ser Glu Gly Glu Thr Leu Ile Ala Arg Leu Ile Asp
                85                  90                  95
Arg Pro Ile Arg Pro Leu Phe Pro Glu Gly Phe Val Asn Glu Val Gln
            100                 105                 110
Val Ile Ala Thr Val Val Ser Val Asn Pro Gln Val Asn Pro Asp Ile
        115                 120                 125
Val Ala Met Ile Gly Ala Ser Ala Ala Leu Ser Leu Ser Gly Ile Pro
    130                 135                 140
Phe Asn Gly Pro Ile Gly Ala Ala Arg Val Gly Tyr Ile Asn Asp Gln
145                 150                 155                 160
Tyr Val Leu Asn Pro Thr Gln Asp Glu Leu Lys Glu Ser Lys Leu Asp
                165                 170                 175
Leu Val Val Ala Gly Thr Glu Ala Ala Val Leu Met Val Glu Ser Glu
            180                 185                 190
Ala Gln Leu Leu Ser Glu Asp Gln Met Leu Gly Ala Val Val Phe Gly
        195                 200                 205
His Glu Gln Gln Gln Val Val Ile Gln Asn Ile Asn Glu Leu Val Lys
    210                 215                 220
```

```
Glu Ala Gly Lys Pro Arg Trp Asp Trp Gln Pro Glu Pro Val Asn Glu
225                 230                 235                 240

Ala Leu Asn Ala Arg Val Ala Ala Leu Ala Glu Ala Arg Leu Ser Asp
            245                 250                 255

Ala Tyr Arg Ile Thr Asp Lys Gln Glu Arg Tyr Ala Gln Val Asp Val
            260                 265                 270

Ile Lys Ser Glu Thr Ile Ala Thr Leu Leu Ala Glu Asp Glu Thr Leu
275                 280                 285

Asp Glu Asn Glu Leu Gly Glu Ile Leu His Ala Ile Glu Lys Asn Val
            290                 295                 300

Val Arg Ser Arg Val Leu Ala Gly Glu Pro Arg Ile Asp Gly Arg Glu
305                 310                 315                 320

Lys Asp Met Ile Arg Gly Leu Asp Val Arg Thr Gly Val Leu Pro Arg
                325                 330                 335

Thr His Gly Ser Ala Leu Phe Thr Arg Gly Glu Thr Gln Ala Leu Val
            340                 345                 350

Thr Ala Thr Leu Gly Thr Ala Arg Asp Ala Gln Val Leu Asp Glu Leu
            355                 360                 365

Met Gly Glu Arg Thr Asp Thr Phe Leu Phe His Tyr Asn Phe Pro Pro
370                 375                 380

Tyr Ser Val Gly Glu Thr Gly Met Val Gly Ser Pro Lys Arg Arg Glu
385                 390                 395                 400

Ile Gly His Gly Arg Leu Ala Lys Arg Gly Val Leu Ala Val Met Pro
                405                 410                 415

Asp Met Asp Lys Phe Pro Tyr Thr Val Arg Val Val Ser Glu Ile Thr
                420                 425                 430

Glu Ser Asn Gly Ser Ser Ser Met Ala Ser Val Cys Gly Ala Ser Leu
            435                 440                 445

Ala Leu Met Asp Ala Gly Val Pro Ile Lys Ala Ala Val Ala Gly Ile
450                 455                 460

Ala Met Gly Leu Val Lys Glu Gly Asp Asn Tyr Val Val Leu Ser Asp
465                 470                 475                 480

Ile Leu Gly Asp Glu Asp His Leu Gly Asp Met Asp Phe Lys Val Ala
                485                 490                 495

Gly Ser Arg Asp Gly Ile Ser Ala Leu Gln Met Asp Ile Lys Ile Glu
                500                 505                 510

Gly Ile Thr Lys Glu Ile Met Gln Val Ala Leu Asn Gln Ala Lys Gly
            515                 520                 525

Ala Arg Leu His Ile Leu Gly Val Met Glu Gln Ala Ile Asn Ala Pro
530                 535                 540

Arg Gly Asp Ile Ser Glu Phe Ala Pro Arg Ile His Thr Ile Lys Ile
545                 550                 555                 560

Asn Pro Asp Lys Ile Lys Asp Val Ile Gly Lys Gly Gly Ser Val Ile
                565                 570                 575

Arg Ala Leu Thr Glu Glu Thr Gly Thr Thr Ile Glu Ile Glu Asp Asp
            580                 585                 590

Gly Thr Val Lys Ile Ala Ala Thr Asp Gly Glu Lys Ala Lys His Ala
            595                 600                 605

Ile Arg Arg Ile Glu Glu Ile Thr Ala Glu Ile Glu Val Gly Arg Val
        610                 615                 620

Tyr Thr Gly Lys Val Thr Arg Ile Val Asp Phe Gly Ala Phe Val Ala
625                 630                 635                 640
```

Ile Gly Gly Gly Lys Glu Gly Leu Val His Ile Ser Gln Ile Ala Asp
            645                 650                 655

Lys Arg Val Glu Lys Val Thr Asp Tyr Leu Gln Met Gly Gln Glu Val
        660                 665                 670

Pro Val Lys Val Leu Glu Val Asp Arg Gln Gly Arg Ile Arg Leu Ser
    675                 680                 685

Ile Lys Glu Ala Thr Glu Gln Ser Gln Pro Ala Ala Ala Pro Glu Ala
690                 695                 700

Pro Ala Ala Glu Gln Gly Glu
705                 710

<210> SEQ ID NO 7
<211> LENGTH: 400
<212> TYPE: PRT
<213> ORGANISM: Xenopus laevis

<400> SEQUENCE: 7

Met Lys Ser Pro Gln Val Glu Cys Lys Glu Ser Met Ser Pro Leu Arg
1               5                   10                  15

Ile Ser Val Ala Gly Leu Pro Val Leu Ala Ser Met Thr Lys Thr Ala
            20                  25                  30

Asp Pro Arg Phe Arg Pro Arg Trp Arg Ala Ile Leu Leu Ser Gly Ile
        35                  40                  45

Ala Val Ala Phe Leu Leu Leu Leu Cys Tyr His Arg Ser Ser Gly
    50                  55                  60

Pro Arg Ile Gln Val Ala Asn Pro His Asn Trp Arg Met Val His Gln
65                  70                  75                  80

Val Ala Gly Glu Leu Tyr Asn Asp Thr Tyr Pro Leu Thr Pro Pro Leu
                85                  90                  95

Arg Thr Pro Glu Gly Leu Arg Tyr His Ile Ala Ile Ala Asp Leu
            100                 105                 110

Asp Thr Asp Ser Arg Ser Ala Lys Ala Asn Thr Trp Val Ser Tyr Leu
        115                 120                 125

Lys Arg Gly Tyr Leu Thr Leu Ser Ser Ser Gly Asp His Val Ala Val
    130                 135                 140

Glu Trp Glu Lys Glu Asp Ile Val Leu Glu Thr His Leu Ala Glu Lys
145                 150                 155                 160

Gly Arg Gly Met Glu Leu Ser Glu Leu Ile Val Phe Asn Gly Lys Leu
                165                 170                 175

Tyr Ser Val Asp Asp Arg Thr Gly Val Val Tyr Arg Ile Glu Gly Ser
            180                 185                 190

Lys Ala Val Pro Trp Val Ile Leu Thr Asp Gly Asp Gly Thr Val Gly
        195                 200                 205

Lys Gly Phe Lys Ala Glu Trp Leu Ala Val Lys Asp Glu Gln Leu Tyr
    210                 215                 220

Val Gly Gly Leu Gly Lys Glu Trp Thr Thr Thr Ser Gly Val Val Leu
225                 230                 235                 240

Asn Glu Asn Pro Glu Trp Val Lys Val Ile Gly Pro Arg Gly Asp Thr
                245                 250                 255

Gln His His Asn Trp Val Ser Asn Tyr Asn Gln Leu Arg Ser Ala Ala
            260                 265                 270

Gly Ile Gln Pro Pro Gly Tyr Leu Ile His Glu Ser Ala Ala Trp Ser
        275                 280                 285

Asp Ser Leu Lys Ser Trp Phe Phe Leu Pro Arg Arg Ala Ser Gln Glu
    290                 295                 300

```
Gln Tyr Ser Glu Lys Glu Asp Glu Lys Arg Gly Ser Asn Ile Leu Leu
305                 310                 315                 320

Arg Ala Thr Pro Asp Phe Ser Asp Ile Lys Met Ser His Val Gly Thr
            325                 330                 335

Leu Asn Pro Thr His Gly Phe Ser Phe Lys Phe Ile Pro Gly Thr
            340                 345                 350

Asp Asp Gln Ile Ile Val Ala Leu Lys Ser Glu Glu Asp Asn Gly Lys
            355                 360                 365

Val Ala Thr Tyr Ile Thr Ala Phe Thr Leu Asp Gly Arg Ile Leu Leu
        370                 375                 380

Pro Glu Thr Lys Val Gly Asn Val Lys Tyr Glu Gly Ile Glu Phe Ile
385                 390                 395                 400

<210> SEQ ID NO 8
<211> LENGTH: 356
<212> TYPE: PRT
<213> ORGANISM: Rat pancreas

<400> SEQUENCE: 8

Leu Ser Gly Ile Ala Val Ala Phe Leu Leu Leu Leu Cys Tyr His
1               5                   10                  15

Arg Ser Ser Gly Pro Arg Ile Gln Val Ala Asn Pro His Asn Trp Arg
            20                  25                  30

Met Val His Gln Val Ala Gly Glu Leu Tyr Asn Asp Thr Tyr Pro Leu
        35                  40                  45

Thr Pro Pro Leu Arg Thr Pro Glu Gly Leu Arg Tyr His Ile Ala Ile
    50                  55                  60

Ile Ala Asp Leu Asp Thr Asp Ser Arg Ser Ala Lys Ala Asn Thr Trp
65                  70                  75                  80

Val Ser Tyr Leu Lys Arg Gly Tyr Leu Thr Leu Ser Ser Ser Gly Asp
                85                  90                  95

His Val Ala Val Glu Trp Glu Lys Glu Asp Ile Val Leu Glu Thr His
            100                 105                 110

Leu Ala Glu Lys Gly Arg Gly Met Glu Leu Ser Glu Leu Ile Val Phe
        115                 120                 125

Asn Gly Lys Leu Tyr Ser Val Asp Asp Arg Thr Gly Val Val Tyr Arg
    130                 135                 140

Ile Glu Gly Ser Lys Ala Val Pro Trp Val Ile Leu Thr Asp Gly Asp
145                 150                 155                 160

Gly Thr Val Gly Lys Gly Phe Lys Ala Glu Trp Leu Ala Val Lys Asp
                165                 170                 175

Glu Gln Leu Tyr Val Gly Gly Leu Gly Lys Glu Trp Thr Thr Thr Ser
            180                 185                 190

Gly Val Val Leu Asn Glu Asn Pro Glu Trp Val Lys Val Ile Gly Pro
        195                 200                 205

Arg Gly Asp Thr Gln His His Asn Trp Val Ser Asn Tyr Asn Gln Leu
    210                 215                 220

Arg Ser Ala Ala Gly Ile Gln Pro Pro Gly Tyr Leu Ile His Glu Ser
225                 230                 235                 240

Ala Ala Trp Ser Asp Ser Leu Lys Ser Trp Phe Phe Leu Pro Arg Arg
                245                 250                 255

Ala Ser Gln Glu Gln Tyr Ser Glu Lys Glu Asp Glu Lys Arg Gly Ser
            260                 265                 270

Asn Ile Leu Leu Arg Ala Thr Pro Asp Phe Ser Asp Ile Lys Met Ser
```

```
                275                 280                 285
His Val Gly Thr Leu Asn Pro Thr His Gly Phe Ser Ser Phe Lys Phe
        290                 295                 300
Ile Pro Gly Thr Asp Asp Gln Ile Ile Val Ala Leu Lys Ser Glu Glu
305                 310                 315                 320
Asp Asn Gly Lys Val Ala Thr Tyr Ile Thr Ala Phe Thr Leu Asp Gly
                325                 330                 335
Arg Ile Leu Leu Pro Glu Thr Lys Val Gly Asn Val Lys Tyr Glu Gly
                340                 345                 350
Ile Glu Phe Ile
        355

<210> SEQ ID NO 9
<211> LENGTH: 697
<212> TYPE: PRT
<213> ORGANISM: Toxoplasma gondii

<400> SEQUENCE: 9

Met Leu Ser Ala Ala Ser Pro Ala Leu Ala Arg Lys Ser Phe Asp Phe
1               5                   10                  15
Arg Gly Ser Ala Leu Arg His Phe Ser Ser Gly Gly His Arg Gly
                20                  25                  30
Ser Ser Asp Thr Lys Ile Ser Pro Gly His Ser Asp Lys Ser Gly Glu
            35                  40                  45
Pro Leu Asp Leu Pro Val Phe Thr Ser Thr Lys Gln Ile Ala Thr Ile
    50                  55                  60
Gly Pro Ala Ser Trp Asp Tyr Glu Glu Ile Glu Arg Leu Phe Leu Ala
65                  70                  75                  80
Gly Val Asp Val Phe Arg Leu Asn Met Ser His Gly Leu Leu Thr Glu
                85                  90                  95
Lys His Gln Gln Leu Leu His Val Arg His Leu Glu Lys Val Tyr Lys
            100                 105                 110
His Pro Ile Ala Val Leu Ala Asp Leu Pro Gly Pro Lys Phe Arg Leu
        115                 120                 125
Gly Val Phe Asn Asn Asp Glu Ala Thr Leu Glu Thr Gly Lys Ser Phe
    130                 135                 140
Ile Leu Asp Ser Ser Thr Gln Pro Gly Asp Ala Ser Arg Val Gln Leu
145                 150                 155                 160
Pro His Pro Glu Ile Leu Ser Val Leu Arg Pro Asp Ile Val Leu
                165                 170                 175
Met Asp Asp Gly Lys Val Lys Leu Arg Val Thr Glu Val Phe Ala Asp
                180                 185                 190
Thr Thr Ala Leu Ser Arg Gly Leu Gly Asp Ile Glu Ser Val Ser His
        195                 200                 205
Thr Ala Ser Pro Gly Ser Ser Val Val Arg Ala Pro Ala Val Arg Cys
    210                 215                 220
Thr Val Leu Val Gly Gly Arg Ile Ser Ser Lys Lys Gly Val Asn Val
225                 230                 235                 240
Pro Ser Ala Arg Leu Pro Ile Ser Ala Leu Ser Ala Arg Asp Arg Glu
                245                 250                 255
Leu Ala Arg Thr Val Ala Ser Trp Gly Val Asp Trp Ile Ala Leu Ser
            260                 265                 270
Phe Val Gln Ser Ala Asp Asp Val His Glu Leu Arg Arg Glu Leu Arg
        275                 280                 285
```

```
Glu Ala Ala Glu Ala Ala Gly Ser Thr Thr Ala Gln Tyr Ala Ala Glu
    290             295                 300

Gln Asn Arg Ser Glu Ser His Val Asp Arg Gly Asp Ala Ser Gly Ala
305             310                 315                 320

Gly Cys Arg Ile Arg Pro Asp Ile Ser Val Met Val Lys Ile Glu Lys
                325                 330                 335

Pro Ile Ala Leu Glu Asn Ile Ala Glu Ile Val Ala Ala Asp Gly
        340                 345                 350

Ile Met Val Ala Arg Gly Asp Leu Gly Val Glu Leu Pro Asn Ile Ala
                355                 360                 365

Trp Leu Pro Arg Val Gln Lys Arg Leu Val Ser Leu Cys Arg Glu Ala
    370                 375                 380

Gly Lys Pro Val Val Ala Thr Gln Met Leu Glu Ser Met Met Gln
385                 390                 395                 400

Ala Pro Leu Pro Thr Arg Ala Glu Val Ser Asp Val Ala Asn Ala Val
            405                 410                 415

Tyr Asp Gly Ala Asp Ala Val Met Leu Ser Gly Glu Thr Ala Ala Gly
                420                 425                 430

Asn Ala Pro Ala Arg Val Ala Cys Met Gln Arg Leu Gly Ile Glu Gly
            435                 440                 445

Val Glu Asn Asp Pro Ser Phe Trp Glu Leu Glu Asp Gln Arg Arg Gln
450                 455                 460

Ala Arg Leu Arg Ala Ala Glu Arg Cys Ala Ser Thr Gly Thr Ser Ala
465             470                 475                 480

Leu Arg Val Pro Arg Ala Ser Lys Gly Arg Glu Gln Glu Leu Glu Lys
                485                 490                 495

Gly Ser Glu Leu Gln Gly Glu Ser Arg Asp Arg Thr Glu Glu Ile Leu
                500                 505                 510

Ser Arg Phe Leu Pro Gly Arg Glu His Leu Ala Phe Ser Glu Ala
            515                 520                 525

Asp Arg Gln Gly Asn Thr Ser Gly Asp Thr Asn Gln Gly Thr Ser Lys
        530                 535                 540

Thr Glu Gln Gly Ala Asp Glu Ser Asp Ala Trp Val Glu His Thr Ala
545                 550                 555                 560

Ala Ala Val Ala Arg Gln Ser Gly Ala Lys Ala Ile Val Val Phe Gly
                565                 570                 575

Glu Asn Glu Ala Leu Leu Gln Arg Leu Ala Thr Leu Arg Pro Thr Ala
            580                 585                 590

Pro Val Leu Ala Val Thr Glu Cys Val His Thr Ala Arg Arg Leu Lys
        595                 600                 605

Met Tyr Trp Gly Ile Tyr Pro Val Leu Leu Glu Ala Glu Asp Gln Ala
    610                 615                 620

Asn Val Glu Ser Arg Ala Arg Arg Pro Ala Ser Leu Asp Asp Gln Leu
625                 630                 635                 640

Arg Leu Ala Cys Glu Phe Ala Arg Lys Glu Lys Phe Ala Thr Glu Ser
                645                 650                 655

Thr Asp Asn Leu Val Val Leu Gly Arg Leu Pro Gly Gly Arg Glu Asn
            660                 665                 670

Gly Thr Asn Ser Asp Lys Thr Thr Ala Arg Leu Thr Arg Pro Ile Leu
                675                 680                 685

Thr Val Cys Thr Leu Glu Ser Gly Arg
    690                 695
```

```
<210> SEQ ID NO 10
<211> LENGTH: 613
<212> TYPE: PRT
<213> ORGANISM: Arabidopsis

<400> SEQUENCE: 10

Met Ala Ser Thr Val Asp Ser Asn Phe Phe Ser Ser Val Pro Ala Leu
1               5                   10                  15

His Ser Asn Leu Gly Leu Leu Ser Pro Asp Gln Ile Glu Leu Ala Lys
            20                  25                  30

Ile Leu Leu Glu Asn Gly Gln Ser His Leu Phe Gln Gln Trp Pro Glu
        35                  40                  45

Leu Gly Val Asp Asp Lys Glu Lys Leu Ala Phe Asp Gln Ile Ala
    50                  55                  60

Arg Leu Asn Ser Ser Tyr Pro Gly Gly Leu Ala Ala Tyr Ile Lys Thr
65                  70                  75                  80

Ala Lys Glu Leu Leu Ala Asp Ser Lys Val Gly Lys Asn Pro Tyr Asp
                85                  90                  95

Gly Phe Ser Pro Ser Val Pro Ser Gly Glu Asn Leu Thr Phe Gly Thr
            100                 105                 110

Asp Asn Phe Ile Glu Met Glu Lys Arg Gly Val Val Glu Ala Arg Asn
        115                 120                 125

Ala Ala Phe Val Leu Val Ala Gly Gly Leu Gly Glu Arg Leu Gly Tyr
130                 135                 140

Asn Gly Ile Lys Val Ala Leu Pro Arg Glu Thr Thr Thr Gly Thr Cys
145                 150                 155                 160

Phe Leu Gln His Tyr Ile Glu Ser Ile Leu Ala Leu Gln Glu Ala Ser
                165                 170                 175

Asn Lys Ile Asp Ser Asp Gly Ser Glu Arg Asp Ile Pro Phe Ile Ile
            180                 185                 190

Met Thr Ser Asp Asp Thr His Ser Arg Thr Leu Asp Leu Leu Glu Leu
        195                 200                 205

Asn Ser Tyr Phe Gly Met Lys Pro Thr Gln Val His Leu Leu Lys Gln
    210                 215                 220

Glu Lys Val Ala Cys Leu Asp Asp Asn Asp Ala Arg Leu Ala Leu Asp
225                 230                 235                 240

Pro His Asn Lys Tyr Ser Ile Gln Thr Lys Pro His Gly His Gly Asp
                245                 250                 255

Val His Ser Leu Leu Tyr Ser Ser Gly Leu Leu His Lys Trp Leu Glu
            260                 265                 270

Ala Gly Leu Lys Trp Val Leu Phe Gln Asp Thr Asn Gly Leu Leu
        275                 280                 285

Phe Asn Ala Ile Pro Ala Ser Leu Gly Val Ser Ala Thr Lys Gln Tyr
    290                 295                 300

His Val Asn Ser Leu Ala Val Pro Arg Lys Ala Lys Glu Ala Ile Gly
305                 310                 315                 320

Gly Ile Ser Lys Leu Thr His Val Asp Gly Arg Ser Met Val Ile Asn
                325                 330                 335

Val Glu Tyr Asn Gln Leu Asp Pro Leu Leu Arg Ala Ser Gly Phe Pro
            340                 345                 350

Asp Gly Asp Val Asn Cys Glu Thr Gly Phe Ser Pro Phe Pro Gly Asn
        355                 360                 365

Ile Asn Gln Leu Ile Leu Glu Leu Gly Pro Tyr Lys Asp Glu Leu Gln
    370                 375                 380
```

```
Lys Thr Gly Gly Ala Ile Lys Glu Phe Val Asn Pro Lys Tyr Lys Asp
385                 390                 395                 400

Ser Thr Lys Thr Ala Phe Lys Ser Ser Thr Arg Leu Glu Cys Met Met
            405                 410                 415

Gln Asp Tyr Pro Lys Thr Leu Pro Pro Thr Ala Arg Val Gly Phe Thr
        420                 425                 430

Val Met Asp Ile Trp Leu Ala Tyr Ala Pro Val Lys Asn Asn Pro Glu
    435                 440                 445

Asp Ala Lys Val Pro Lys Gly Asn Pro Tyr His Ser Ala Thr Ser
    450                 455                 460

Gly Glu Met Ala Ile Tyr Arg Ala Asn Ser Leu Ile Leu Gln Lys Ala
465                 470                 475                 480

Gly Val Lys Val Glu Glu Pro Val Lys Gln Val Leu Asn Gly Gln Glu
            485                 490                 495

Val Glu Val Trp Ser Arg Ile Thr Trp Lys Pro Lys Trp Gly Met Ile
        500                 505                 510

Phe Ser Asp Ile Lys Lys Val Ser Gly Asn Cys Glu Val Ser Gln
    515                 520                 525

Arg Ser Thr Met Ala Ile Lys Gly Arg Asn Val Phe Ile Lys Asp Leu
530                 535                 540

Ser Leu Asp Gly Ala Leu Ile Val Asp Ser Ile Asp Ala Glu Val
545                 550                 555                 560

Lys Leu Gly Gly Leu Ile Asn Asn Gly Trp Thr Met Glu Ser Val Asp
            565                 570                 575

Tyr Lys Asp Thr Ser Val Pro Glu Glu Ile Arg Ile Arg Gly Phe Arg
        580                 585                 590

Phe Asn Lys Val Glu Gln Leu Glu Lys Lys Leu Thr Gln Pro Gly Lys
    595                 600                 605

Phe Ser Val Glu Asp
610

<210> SEQ ID NO 11
<211> LENGTH: 965
<212> TYPE: PRT
<213> ORGANISM: Pasteurella multocida

<400> SEQUENCE: 11

Met Asn Thr Leu Ser Gln Ala Ile Lys Ala Tyr Asn Ser Asn Asp Tyr
1               5                   10                  15

Glu Leu Ala Leu Lys Leu Phe Glu Lys Ser Ala Glu Thr Tyr Gly Arg
            20                  25                  30

Lys Ile Val Glu Phe Gln Ile Ile Lys Cys Lys Glu Lys Leu Ser Thr
        35                  40                  45

Asn Ser Tyr Val Ser Glu Asp Lys Lys Asn Ser Val Cys Asp Ser Ser
    50                  55                  60

Leu Asp Ile Ala Thr Gln Leu Leu Ser Asn Val Lys Lys Leu Thr
65                  70                  75                  80

Leu Ser Glu Ser Glu Lys Asn Ser Leu Lys Asn Lys Trp Lys Ser Ile
            85                  90                  95

Thr Gly Lys Lys Ser Glu Asn Ala Glu Ile Arg Lys Val Glu Leu Val
        100                 105                 110

Pro Lys Asp Phe Pro Lys Asp Leu Val Leu Ala Pro Leu Pro Asp His
    115                 120                 125

Val Asn Asp Phe Thr Trp Tyr Lys Asn Arg Lys Lys Ser Leu Gly Ile
    130                 135                 140
```

```
Lys Pro Val Asn Lys Asn Ile Gly Leu Ser Ile Ile Pro Thr Phe
145                 150                 155                 160

Asn Arg Ser Arg Ile Leu Asp Ile Thr Leu Ala Cys Leu Val Asn Gln
            165                 170                 175

Lys Thr Asn Tyr Pro Phe Glu Val Val Ala Asp Asp Gly Ser Lys
        180                 185                 190

Glu Asn Leu Leu Thr Ile Val Gln Lys Tyr Glu Gln Lys Leu Asp Ile
            195                 200                 205

Lys Tyr Val Arg Gln Lys Asp Tyr Gly Tyr Gln Leu Cys Ala Val Arg
210                 215                 220

Asn Leu Gly Leu Arg Thr Ala Lys Tyr Asp Phe Val Ser Ile Leu Asp
225                 230                 235                 240

Cys Asp Met Ala Pro Gln Gln Leu Trp Val His Ser Tyr Leu Thr Glu
                245                 250                 255

Leu Leu Glu Asp Asn Asp Ile Val Leu Ile Gly Pro Arg Lys Tyr Val
            260                 265                 270

Asp Thr His Asn Ile Thr Ala Glu Gln Phe Leu Asn Asp Pro Tyr Leu
        275                 280                 285

Ile Glu Ser Leu Pro Glu Thr Ala Thr Asn Asn Pro Ser Ile Thr
290                 295                 300

Ser Lys Gly Asn Ile Ser Leu Asp Trp Arg Leu Glu His Phe Lys Lys
305                 310                 315                 320

Thr Asp Asn Leu Arg Leu Cys Asp Ser Pro Phe Arg Tyr Phe Ser Cys
                325                 330                 335

Gly Asn Val Ala Phe Ser Lys Glu Trp Leu Asn Lys Val Gly Trp Phe
            340                 345                 350

Asp Glu Glu Phe Asn His Trp Gly Gly Glu Asp Val Glu Phe Gly Tyr
        355                 360                 365

Arg Leu Phe Ala Lys Gly Cys Phe Phe Arg Val Ile Asp Gly Gly Met
370                 375                 380

Ala Tyr His Gln Glu Pro Pro Gly Lys Glu Asn Glu Thr Asp Arg Glu
385                 390                 395                 400

Ala Gly Lys Ser Ile Thr Leu Lys Ile Val Lys Glu Lys Val Pro Tyr
                405                 410                 415

Ile Tyr Arg Lys Leu Leu Pro Ile Glu Asp Ser His Ile His Arg Ile
            420                 425                 430

Pro Leu Val Ser Ile Tyr Ile Pro Ala Tyr Asn Cys Ala Asn Tyr Ile
        435                 440                 445

Gln Arg Cys Val Asp Ser Ala Leu Asn Gln Thr Val Val Asp Leu Glu
        450                 455                 460

Val Cys Ile Cys Asn Asp Gly Ser Thr Asp Asn Thr Leu Glu Val Ile
465                 470                 475                 480

Asn Lys Leu Tyr Gly Asn Asn Pro Arg Val Arg Ile Met Ser Lys Pro
                485                 490                 495

Asn Gly Gly Ile Ala Ser Ala Ser Asn Ala Ala Val Ser Phe Ala Lys
            500                 505                 510

Gly Tyr Tyr Ile Gly Gln Leu Asp Ser Asp Tyr Leu Glu Pro Asp
        515                 520                 525

Ala Val Glu Leu Cys Leu Lys Glu Phe Leu Lys Asp Lys Thr Leu Ala
            530                 535                 540

Cys Val Tyr Thr Thr Asn Arg Asn Val Asn Pro Asp Gly Ser Leu Ile
545                 550                 555                 560
```

-continued

```
Ala Asn Gly Tyr Asn Trp Pro Glu Phe Ser Arg Glu Lys Leu Thr Thr
                565                 570                 575
Ala Met Ile Ala His His Phe Arg Met Phe Thr Ile Arg Ala Trp His
            580                 585                 590
Leu Thr Asp Gly Phe Asn Glu Asn Ile Glu Asn Ala Val Asp Tyr Asp
        595                 600                 605
Met Phe Leu Lys Leu Ser Glu Val Gly Lys Phe Lys His Leu Asn Lys
    610                 615                 620
Ile Cys Tyr Asn Arg Val Leu His Gly Asp Asn Thr Ser Ile Lys Lys
625                 630                 635                 640
Leu Gly Ile Gln Lys Lys Asn His Phe Val Val Asn Gln Ser Leu
                645                 650                 655
Asn Arg Gln Gly Ile Asn Tyr Tyr Asn Tyr Asp Lys Phe Asp Asp Leu
            660                 665                 670
Asp Glu Ser Arg Lys Tyr Ile Phe Asn Lys Thr Ala Glu Tyr Gln Glu
        675                 680                 685
Glu Met Asp Ile Leu Lys Asp Leu Lys Leu Ile Gln Asn Lys Asp Ala
    690                 695                 700
Lys Ile Ala Val Ser Ile Phe Tyr Pro Asn Thr Leu Asn Gly Leu Val
705                 710                 715                 720
Lys Lys Leu Asn Asn Ile Ile Glu Tyr Asn Lys Asn Ile Phe Val Ile
                725                 730                 735
Ile Leu His Val Asp Lys Asn His Leu Thr Pro Asp Ile Lys Lys Glu
            740                 745                 750
Ile Leu Ala Phe Tyr His Lys His Gln Val Asn Ile Leu Leu Asn Asn
        755                 760                 765
Asp Ile Ser Tyr Tyr Thr Ser Asn Arg Leu Ile Lys Thr Glu Ala His
    770                 775                 780
Leu Ser Asn Ile Asn Lys Leu Ser Gln Leu Asn Leu Asn Cys Glu Tyr
785                 790                 795                 800
Ile Ile Phe Asp Asn His Asp Ser Leu Phe Val Lys Asn Asp Ser Tyr
                805                 810                 815
Ala Tyr Met Lys Lys Tyr Asp Val Gly Met Asn Phe Ser Ala Leu Thr
            820                 825                 830
His Asp Trp Ile Glu Lys Ile Asn Ala His Pro Pro Phe Lys Lys Leu
        835                 840                 845
Ile Lys Thr Tyr Phe Asn Asp Asn Asp Leu Arg Ser Met Asn Val Lys
    850                 855                 860
Gly Ala Ser Gln Gly Met Phe Met Lys Tyr Ala Leu Pro His Glu Leu
865                 870                 875                 880
Leu Thr Ile Ile Lys Glu Val Ile Thr Ser Cys Gln Ser Ile Asp Ser
                885                 890                 895
Val Pro Glu Tyr Asn Thr Glu Asp Ile Trp Phe Gln Phe Ala Leu Leu
            900                 905                 910
Ile Leu Glu Lys Lys Thr Gly His Val Phe Asn Lys Ser Thr Leu
        915                 920                 925
Thr Tyr Met Pro Trp Glu Arg Lys Leu Gln Trp Thr Asn Glu Gln Ile
    930                 935                 940
Gln Ser Ala Lys Lys Gly Glu Asn Ile Pro Val Asn Lys Phe Ile Ile
945                 950                 955                 960
Asn Ser Ile Thr Leu
                965
```

<210> SEQ ID NO 12
<211> LENGTH: 1596
<212> TYPE: PRT
<213> ORGANISM: Acetobacter xylinum

<400> SEQUENCE: 12

Met Ile Tyr Arg Ala Ile Leu Lys Arg Leu Arg Leu Glu Gln Leu Ala
1               5                   10                  15

Arg Val Pro Ala Val Ser Ala Ser Pro Phe Val Met Met Ala Val
            20                  25                  30

Gly Val Phe Leu Met Leu Met Ala Gly Gly Val Thr Ile Ser Thr Thr
            35                  40                  45

Ser Gln Ala Phe Val Thr Cys Gly Thr Val Gly Leu Phe Leu Leu Leu
        50                  55                  60

Lys Gly Arg Lys Gly Arg Gly Val Thr Cys Phe Leu Met Met Leu Ser
65                  70                  75                  80

Leu Leu Val Ser Leu Arg Tyr Met Val Trp Arg Leu Thr Thr Thr Leu
                85                  90                  95

Glu Leu His Ser Pro Leu Gln Ala Ala Leu Ser Leu Leu Val Ala
            100                 105                 110

Ala Glu Leu Tyr Ala Leu Leu Thr Leu Cys Leu Ser Tyr Phe Gln Met
            115                 120                 125

Ser Trp Pro Leu Asp Arg Lys Pro Leu Pro Leu Pro Ala Asp Thr Thr
        130                 135                 140

Asp Trp Pro Val Val Asp Val Tyr Val Pro Ser Tyr Asn Glu Glu Leu
145                 150                 155                 160

Ser Leu Val Arg Ser Thr Val Leu Gly Ala Leu Ala Ile Asp Trp Pro
                165                 170                 175

Ala Asp Lys Leu Asn Val Tyr Ile Leu Asp Asp Gly Arg Arg Lys Ser
            180                 185                 190

Phe His Ala Phe Ala Met Glu Ala Gly Ala Gly Tyr Ile Ile Arg Asp
            195                 200                 205

Gln Asn Asn His Ala Lys Ala Gly Asn Leu Asn His Ala Leu Arg Val
        210                 215                 220

Thr Glu Gly Glu Tyr Val Val Ile Phe Asp Cys Asp His Ile Pro Thr
225                 230                 235                 240

Arg Gly Phe Leu Lys Lys Thr Ile Gly Trp Met Met Ala Asp Pro Lys
                245                 250                 255

Leu Ala Leu Leu Gln Thr Pro His His Phe Tyr Ser Pro Asp Pro Phe
            260                 265                 270

Gln Arg Asn Leu Ala Thr Gly Gln Asn Val Pro Pro Glu Gly Asn Met
            275                 280                 285

Phe Tyr Gly Leu Val Gln Asp Gly Asn Asp Phe Trp Asp Ala Thr Phe
        290                 295                 300

Phe Cys Gly Ser Cys Ala Ala Ile Arg Arg Ser Ala Val Leu Gly Ile
305                 310                 315                 320

Gly Gly Phe Ala Thr Glu Thr Val Thr Glu Asp Ala His Thr Ala Leu
                325                 330                 335

Lys Met Gln Arg Glu Gly Trp His Thr Ala Tyr Leu Arg Gln Pro Leu
            340                 345                 350

Ala Ala Gly Leu Ser Thr Glu Arg Leu Met Leu His Ile Gly Gln Arg
        355                 360                 365

Val Arg Trp Ala Arg Gly Met Leu Gln Ile Met Arg Leu Asp Asn Pro
    370                 375                 380

```
Leu Leu Gly Ser Gly Leu Arg Trp Gln Gln Arg Leu Cys Tyr Leu Ser
385                 390                 395                 400

Ala Met Ser His Phe Leu Phe Ala Ile Pro Arg Leu Val Phe Leu Ala
            405                 410                 415

Ser Pro Leu Ala Phe Leu Phe Leu Gly Gln Asn Ile Ile Ala Ala Ser
            420                 425                 430

Pro Phe Ala Ile Leu Val Tyr Ala Phe Pro His Val Phe His Ser Ile
            435                 440                 445

Gly Thr Leu Ser Arg Val Glu Gly Arg Trp Arg Tyr Ser Phe Trp Ser
    450                 455                 460

Glu Ile Tyr Glu Thr Thr Leu Ala Leu Phe Leu Val Arg Val Thr Ile
465                 470                 475                 480

Met Thr Leu Leu Asn Pro Arg Lys Gly Glu Phe Asn Val Thr Asp Lys
            485                 490                 495

Gly Gly Leu Leu Gln Ser Glu Tyr Phe Asp Leu Asn Ala Val Tyr Pro
            500                 505                 510

Asn Val Ile Leu Ala Val Ile Leu Ala Leu Ala Leu Val Arg Gly Ile
            515                 520                 525

Gly Gly Met Met Trp Glu Tyr His Asp Arg Leu Ala Leu Gln Ser Phe
    530                 535                 540

Ala Leu Asn Thr Leu Trp Val Ala Val Ser Leu Ile Ile Val Leu Ala
545                 550                 555                 560

Ser Ile Ala Val Gly Arg Glu Thr Arg Gln Ile Arg His Lys Pro Arg
            565                 570                 575

Val Arg Ala Thr Leu Pro Ile Thr Leu Ile Asp Glu His Gly Gln His
            580                 585                 590

Tyr His Ala His Thr Ser Asp Ile Ser Leu Gly Gly Ile Ala Ala Arg
    595                 600                 605

Leu Ser Thr Glu His Ala Leu Pro Thr Gln Thr Arg Val Thr Met Leu
            610                 615                 620

Tyr His Asn Glu Lys Asp Gly Ile Asp Val Arg Ile Pro Ala Val Ile
625                 630                 635                 640

Leu Phe Ser Lys Pro Gly Gln Leu His Leu Gln Trp Ser Val Asp Asp
            645                 650                 655

Leu Asp Val Glu Arg Gln Ile Val Glu Phe Met Phe Gly Arg Asn Asp
            660                 665                 670

Ala Trp Ser Asn Trp Gly Asp Phe Gln Pro Asp Arg Pro Val Arg Ser
    675                 680                 685

Phe Leu Met Val Leu Arg Ser Ile Gly Gly Leu Phe Arg Arg Gly Gln
            690                 695                 700

Arg Leu Phe Arg Trp Gln Ala Pro Gln Glu Ala Pro Leu Ala Glu Ser
705                 710                 715                 720

Glu His Val Glu Glu Lys Leu Glu Lys Lys Ser Leu Val Leu Lys
            725                 730                 735

Pro Val Arg Arg Ser Ala Arg His Gly Ala Thr Ala Ser Leu Ile Val
            740                 745                 750

Leu Leu Gly Leu Pro Ala Ala Ile Ala Pro Ser Leu Ala Gln Ala Pro
    755                 760                 765

Ser Arg Ala Thr Pro Val Ala Thr Glu Gln Gly Ala Thr Pro Val Glu
            770                 775                 780

Pro Pro Pro Val Asn Ala Pro Pro Pro Ser Leu Pro Gln Pro Pro
785                 790                 795                 800

Gly Thr Leu Pro Thr Pro Pro Gln Ile Ala Pro Ala Ser Ala Gly Glu
```

```
                805                 810                 815
Leu Leu Pro Ala Ala Thr Ala Val Ser Leu Pro Thr Gly Pro Ala Thr
                820                 825                 830

Gln Gln Met Arg Glu Arg Leu Ser Glu Arg Thr Gly Val Ser Pro Ala
                835                 840                 845

Ser Pro Phe Gly Asp Thr Asn Thr Gly Ala Leu Pro Ala Asp Pro Ser
    850                 855                 860

Ala Pro Pro Ile Asp Pro Ala Asp Ala Ala Arg Val Ala Asp Gly Glu
865                 870                 875                 880

Ile Thr Arg Thr Ser Thr Phe Arg Asp Leu Gly Leu Ala Thr Gly Pro
                885                 890                 895

Leu Thr Leu Arg Gly Phe Ser Pro Leu Gln Gly Leu Asp Val Ile Val
                900                 905                 910

Pro Ala Asn Arg Val Val Thr Arg Ala Arg Ile Thr Leu Ser Gly Ala
                915                 920                 925

Leu Ser Pro Ser Leu Leu Pro Glu Ala Ser Ala Val Ser Val Thr Leu
                930                 935                 940

Asn Glu Gln Tyr Val Gly Thr Ile Arg Val Asp Pro Glu His Pro Arg
945                 950                 955                 960

Phe Gly Pro Ile Thr Phe Asp Ile Asp Pro Leu Tyr Phe Thr Gly Asp
                965                 970                 975

Asn Lys Leu Asn Phe His Phe Ala Gly Glu Tyr Arg Arg Asp Cys Asn
                980                 985                 990

Asp Leu Tyr Asn Glu Val Leu Trp Ala Arg Ile Ser Asp Phe Ser Thr
                995                 1000                1005

Val Thr Leu Thr Thr Thr Arg Ile Ala Pro Asp Arg Lys Leu Ser
    1010                1015                1020

Tyr Leu Pro Ala Pro Phe Tyr Asp Pro Asn Leu Arg Thr Pro Leu
    1025                1030                1035

Arg Val Pro Val Val Met Pro Asn Pro Asp Ala His Gly Met Leu
    1040                1045                1050

Lys Ala Ser Ala Leu Val Ala Ser Trp Phe Gly Lys Leu Ala Asp
    1055                1060                1065

Phe Arg Lys Val Ser Phe Pro Val Ser Thr Thr Ile Pro Ala Ser
    1070                1075                1080

Gly Asn Ala Ile Ala Ile Gly Glu Asn Leu Pro Ile Asp Ala Arg
    1085                1090                1095

Gly Thr Arg Pro Thr Gly Pro Thr Leu Ser Glu Val Glu Asn Pro
    1100                1105                1110

Asn Asp Arg Leu Gly Thr Ile Leu Val Leu Thr Gly Arg Asn Ala
    1115                1120                1125

Gln Glu Val Glu Val Ala Ala Arg Val Leu Ala Phe Ser Ser Asp
    1130                1135                1140

Thr Leu Gly Ala Val Gly Thr Lys Val Val Asn Asp Val Thr Leu
    1145                1150                1155

Gln Pro Arg His Pro Tyr Asp Ala Pro Ala Phe Val Pro Thr Asp
    1160                1165                1170

Arg Pro Val Arg Phe Gly Glu Leu Val Ala Ala Ser Asp Leu Gln
    1175                1180                1185

Gly Gly Gly Phe Ala Pro Pro Val Met Ala Leu Pro Phe His Leu
    1190                1195                1200

Pro Pro Asp Leu Tyr Ser Trp Arg Asn Arg Pro Tyr Pro Ile Asp
    1205                1210                1215
```

```
Leu Trp Val Arg Thr Pro Gly Gly Pro Val Val Asp Leu Glu Thr
1220             1225             1230

Ser Arg Leu Asp Val His Leu Asn Asn Asn Tyr Leu Asp Ser Phe
1235             1240             1245

Thr Leu Lys Pro Pro Ser Leu Trp Ala Ala Trp Ser Glu Arg Leu
1250             1255             1260

Val Asn Gln His Ala Gly Ala Val Glu His Ala Ala Ala Leu Pro
1265             1270             1275

Pro Trp Leu Leu Phe Gly Gln Asn Gln Leu Lys Phe Ser Phe Asp
1280             1285             1290

Ala Arg Pro Ile Asp Arg Gly Val Cys Arg Arg Thr Pro Asp Asp
1295             1300             1305

Ile His Met Ser Val Asp Ser Asp Ser Trp Leu Asp Phe Arg Arg
1310             1315             1320

Gly Tyr His Phe Ala Arg Leu Pro Asn Leu Ser Tyr Phe Ala Glu
1325             1330             1335

Ala Ala Phe Pro Phe Ser Arg Met Ala Asp Leu Ser Glu Thr Thr
1340             1345             1350

Val Val Val Pro His His Ile Asp Ala Gly Thr Ala Gly Thr Phe
1355             1360             1365

Met Asp Leu Met Gly Phe Phe Gly Ala Thr Thr Trp Tyr Pro Ala
1370             1375             1380

Ser Gly Val Gln Val Ala Asp Ile Asn Asp Leu Ser Glu His Pro
1385             1390             1395

Pro Gln Gly Asp Ile Leu Ile Leu Ala Thr Ala Gly Asp Ala Pro
1400             1405             1410

Lys Phe Glu Glu Leu Leu Thr Arg Ala Pro Tyr Glu Leu Thr Asp
1415             1420             1425

Gly His Ile Arg Val Gly Gln His Met Gly Leu Gln Gly Ile Trp
1430             1435             1440

Tyr Leu Phe Gln Asp His Asp His Ala Gly Leu Gln Asp Gly Val
1445             1450             1455

Gln Ala Asn Leu Asn Ala Pro Ile Ala Gly Ala Gly Val Leu Leu
1460             1465             1470

Gly Ala Gln Ser Pro Tyr Arg Ser Asp Arg Ser Val Val Ala Leu
1475             1480             1485

Met Gly Asp Thr Pro Ser Arg Met His Asp Leu Val Met Gly Leu
1490             1495             1500

Arg Ser Lys Glu Asp Val Pro Arg Ile Gln Gly Asp Leu Val Leu
1505             1510             1515

Arg Asn Gly Asp Arg Leu Thr Ser Tyr Arg Thr Ala Pro Thr Phe
1520             1525             1530

Thr Met Gly Ser Leu Pro Trp Trp Met Trp Leu Asp Trp Tyr Leu
1535             1540             1545

Gly Thr Arg Pro Leu Thr Leu Tyr Val Leu Gly Leu Val Gly Ala
1550             1555             1560

Gly Leu Val Ala Ala Ala Val Arg Leu Leu Arg Arg Arg Ala
1565             1570             1575

Gln His Arg Leu Glu Glu Ala Ala Arg Val Lys Asp Thr Thr Asp
1580             1585             1590

Ala Ser His
1595
```

<210> SEQ ID NO 13
<211> LENGTH: 705
<212> TYPE: PRT
<213> ORGANISM: Saccharomyces cerevisiae

<400> SEQUENCE: 13

Met Ser Arg Asp Leu Gln Asn His Leu Leu Phe Glu Thr Ala Thr Glu
1               5                   10                  15

Val Ala Asn Arg Val Gly Gly Ile Tyr Ser Val Leu Lys Ser Lys Ala
            20                  25                  30

Pro Ile Thr Val Ala Gln Tyr Lys Asp His Tyr His Leu Ile Gly Pro
        35                  40                  45

Leu Asn Lys Ala Thr Tyr Gln Asn Glu Val Asp Ile Leu Asp Trp Lys
    50                  55                  60

Lys Pro Glu Ala Phe Ser Asp Glu Met Arg Pro Val Gln His Ala Leu
65                  70                  75                  80

Gln Thr Met Glu Ser Arg Gly Val His Phe Val Tyr Gly Arg Trp Leu
                85                  90                  95

Ile Glu Gly Ala Pro Lys Val Ile Leu Phe Asp Leu Asp Ser Val Arg
            100                 105                 110

Gly Tyr Ser Asn Glu Trp Lys Gly Asp Leu Trp Ser Leu Val Gly Ile
        115                 120                 125

Pro Ser Pro Glu Asn Asp Phe Glu Thr Asn Asp Ala Ile Leu Leu Gly
    130                 135                 140

Tyr Thr Val Ala Trp Phe Leu Gly Glu Val Ala His Leu Asp Ser Gln
145                 150                 155                 160

His Ala Ile Val Ala His Phe His Glu Trp Leu Ala Gly Val Ala Leu
                165                 170                 175

Pro Leu Cys Arg Lys Arg Arg Ile Asp Val Val Thr Ile Phe Thr Thr
            180                 185                 190

His Ala Thr Leu Leu Gly Arg Tyr Leu Cys Ala Ser Gly Ser Phe Asp
        195                 200                 205

Phe Tyr Asn Cys Leu Glu Ser Val Asp Val Asp His Glu Ala Gly Arg
    210                 215                 220

Phe Gly Ile Tyr His Arg Tyr Cys Ile Glu Arg Ala Ala His His Ser
225                 230                 235                 240

Ala Asp Val Phe Thr Thr Val Ser Gln Ile Thr Ala Phe Glu Ala Glu
                245                 250                 255

His Leu Leu Lys Arg Lys Pro Asp Gly Ile Leu Pro Asn Gly Leu Asn
            260                 265                 270

Val Ile Lys Phe Gln Ala Phe His Glu Phe Gln Asn Leu His Ala Leu
        275                 280                 285

Lys Lys Glu Lys Ile Asn Asp Phe Val Arg Gly His Phe His Gly Cys
    290                 295                 300

Phe Asp Phe Asp Leu Asp Asn Thr Leu Tyr Phe Phe Ile Ala Gly Arg
305                 310                 315                 320

Tyr Glu Tyr Lys Asn Lys Gly Ala Asp Met Phe Ile Glu Ala Leu Ala
                325                 330                 335

Arg Leu Asn Tyr Arg Leu Lys Val Ser Gly Ser Lys Lys Thr Val Val
            340                 345                 350

Ala Phe Ile Val Met Pro Ala Lys Asn Asn Ser Phe Thr Val Glu Ala
        355                 360                 365

Leu Lys Gly Gln Ala Glu Val Arg Ala Leu Glu Asn Thr Val His Glu
    370                 375                 380

```
Val Thr Thr Ser Ile Gly Lys Arg Ile Phe Asp His Ala Ile Arg Tyr
385             390                 395                 400

Pro His Asn Gly Leu Thr Thr Glu Leu Pro Thr Asp Leu Gly Glu Leu
            405                 410                 415

Leu Lys Ser Ser Asp Lys Val Met Leu Lys Arg Arg Ile Leu Ala Leu
            420                 425                 430

Arg Arg Pro Glu Gly Gln Leu Pro Pro Ile Val Thr His Asn Met Val
            435                 440                 445

Asp Asp Ala Asn Asp Leu Ile Leu Asn Lys Ile Arg Gln Val Gln Leu
        450                 455                 460

Phe Asn Ser Pro Ser Asp Arg Val Lys Met Ile Phe His Pro Glu Phe
465             470                 475                 480

Leu Asn Ala Asn Asn Pro Ile Leu Gly Leu Asp Tyr Asp Glu Phe Val
            485                 490                 495

Arg Gly Cys His Leu Gly Val Phe Pro Ser Tyr Tyr Glu Pro Trp Gly
            500                 505                 510

Tyr Thr Pro Ala Glu Cys Thr Val Met Gly Val Pro Ser Ile Thr Thr
        515                 520                 525

Asn Val Ser Gly Phe Gly Ala Tyr Met Glu Asp Leu Ile Glu Thr Asn
    530                 535                 540

Gln Ala Lys Asp Tyr Gly Ile Tyr Ile Val Asp Arg Arg Phe Lys Ala
545             550                 555                 560

Pro Asp Glu Ser Val Glu Gln Leu Val Asp Tyr Met Glu Glu Phe Val
            565                 570                 575

Lys Lys Thr Arg Arg Gln Arg Ile Asn Gln Arg Asn Arg Thr Glu Arg
            580                 585                 590

Leu Ser Asp Leu Leu Asp Trp Lys Arg Met Gly Leu Glu Tyr Val Lys
        595                 600                 605

Ala Arg Gln Leu Ala Leu Arg Arg Gly Tyr Pro Asp Gln Phe Arg Glu
    610                 615                 620

Leu Val Gly Glu Glu Leu Asn Asp Ser Asn Met Asp Ala Leu Ala Gly
625             630                 635                 640

Gly Lys Lys Leu Lys Val Ala Arg Pro Leu Ser Val Pro Gly Ser Pro
            645                 650                 655

Arg Asp Leu Arg Ser Asn Ser Thr Val Tyr Met Thr Pro Gly Asp Leu
            660                 665                 670

Gly Thr Leu Gln Glu Val Asn Asn Ala Asp Tyr Phe Ser Leu Gly
        675                 680                 685

Val Asn Pro Ala Ala Asp Asp Asp Asp Gly Pro Tyr Ala Asp Asp
    690                 695                 700

Ser
705
```

METHOD FOR PRODUCING POLYSACCHARIDE

TECHNICAL FIELD

The present invention relates to a method for producing a polysaccharide.

BACKGROUND ART

Various types of polysaccharides are known, such as plant-derived polysaccharides (e.g., starch and cellulose), microorganism-derived polysaccharides (e.g., xanthan), and higher organism-derived polysaccharides (e.g., hyaluronan, heparin, and chondroitin). These polysaccharides are used in medicinal products, food products, general industrial applications, and other various applications.

Hyaluronan, for example, is found in high quantity in biological tissues, such as bovine eyes, rooster combs, shock-absorbing tissue of animals, placentas, cancer cells, and skin. Hyaluronan is a linear polysaccharide consisting of alternating glucuronic acid and N-acetylglucosamine bonded by $\beta 1,3$ and $\beta 1,4$ linkages, and is a high molecular weight glucosaminoglycan having a molecular weight of $10^5$ to $10^6$ Da. Hyaluronan is characterized by its high viscosity, high moisturizing effect, excellent lubricating effect against physical friction, and protective effect against bacterial and other invasions.

Because of these characteristics, hyaluronan is widely used as a cosmetic additive and a pharmaceutical additive (e.g., arthritis treatment agent, wound dressing agent, ophthalmic surgery adjuvant, and post-surgery anti-adhesion agent).

Widely known methods for producing hyaluronan include: (1) a method for extracting hyaluronan from the biological tissues (extraction method) (Patent Literatures 1 and 2), and (2) a method for collecting hyaluronan from a culture of microorganisms having an ability to produce hyaluronan in the presence of a sugar such as glucose (microorganism culture method) (Patent Literatures 3 and 4).

Unfortunately, the hyaluronan produced by the extraction method (1) contains impurities such as chondroitin sulfate and glycosaminoglycan sulfate. Hence, a complicated purification process is required in order to remove these impurities.

In the hyaluronan production by the microorganism culture method (2), an increase in the hyaluronan production entails an increase in the viscosity of the culture medium, making it difficult to stir for aeration. As stirring for aeration becomes more difficult, the hyaluronan production will eventually stop. Thus, the microorganism culture method unfortunately has very low hyaluronan production efficiency. In addition, because of the high viscosity of the culture medium, the method requires a complicated purification process in order to remove the microorganisms used. Further, hyaluronan-degrading enzymes present in the microorganisms degrade the produced hyaluronan, causing problems such as no increase in the molecular weight of the hyaluronan and high heterogeneity in the molecular weight.

Also in the case of other polysaccharides besides hyaluronan, the extraction method involves contamination with various impurities, and the microorganism culture method has drawbacks such as low production efficiency, no increase in the molecular weight, and high heterogeneity in the molecular weight.

Thus, a method for producing a polysaccharide using a polysaccharide synthase (enzymatic synthesis method) has been considered as a third method that does not involve biological tissue extraction or microorganism cultivation. For example, a method that uses a hyaluronan synthase is known (Non-Patent Literature 1). Unfortunately, the enzymatic synthesis method has drawbacks such as requirement for a large amount of enzyme, low production efficiency, and a low yield. Thus, the method remains at the laboratory level and its application at the industrial level is yet to be considered.

CITATION LIST

Patent Literature

Patent Literature 1: U.S. Pat. No. 4,141,973
Patent Literature 2: U.S. Pat. No. 4,303,676
Patent Literature 3: JP-A S58-056692
Patent Literature 4: WO 86/04355

Non-Patent Literature

Non-Patent Literature 1: The Journal of Biochemistry, 1998, Vol. 273, No. 14, pp. 8454-8458

SUMMARY OF INVENTION

Technical Problem

The present invention aims to provide a method for producing a polysaccharide with high efficiency using a polysaccharide synthase.

Solution to Problem

The present inventors conducted studies to achieve the above aim, and accomplished the present invention.

Specifically, the present invention provides a method for producing a polysaccharide, including allowing polysaccharide synthase (B) to act on ribonucleoside diphosphate-monosaccharide (A) shown below to produce a polysaccharide, wherein in 10 to 100% of the duration in which (B) acts on (A), the concentration of ribonucleoside diphosphate in a reaction solution is lower than 100 times a inhibitory concentration $IC_{50}$ described below against polysaccharide synthase (B).

Inhibitory concentration $IC_{50}$: a concentration of ribonucleoside diphosphate at which an enzyme activity of polysaccharide synthase (B) is reduced by half under a condition where (B) has a concentration at which (B) acts on ribonucleoside diphosphate-monosaccharide (A), wherein ribonucleoside diphosphate-monosaccharide (A) is used as a substrate and ribonucleoside diphosphate is used as an inhibitor.

Ribonucleoside diphosphate-monosaccharide (A): a sugar nucleotide in which a proton of at least one hydroxyl group of at least one monosaccharide (a) selected from the group consisting of triose (a-1), tetrose (a-2), pentose (a-3), hexose (a-4), heptose (a-5), and monosaccharide (a-6) described below is substituted with a functional group represented by any one of chemical formulae (1) to (5) below:

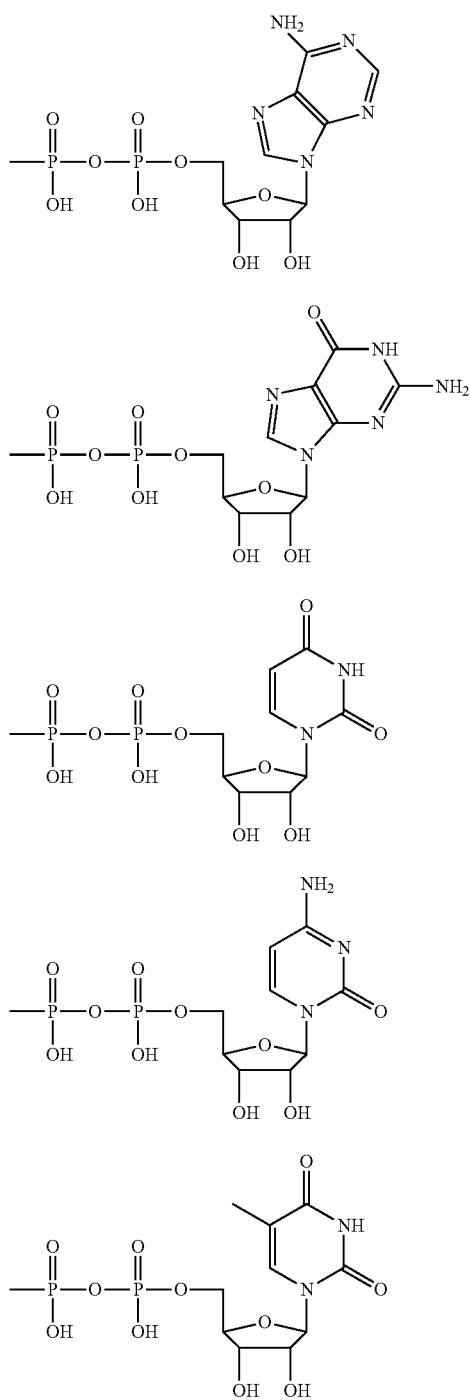

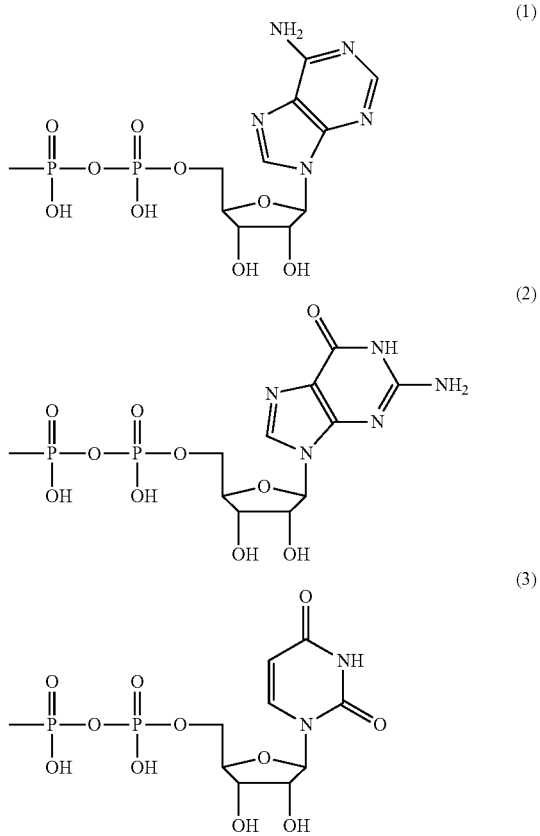

Monosaccharide (a-6): a monosaccharide selected from the group consisting of (a-1), (a-2), (a-3), (a-4), and (a-5), in which at least one member selected from the group consisting of a proton, a hydroxyl group, and a hydroxymethyl group of the monosaccharide is substituted with substituent (E) described below.

Substituent (E): at least one substituent selected from the group consisting of carboxyl, amino, N-acetylamino, sulfate, methylester, N-glycolyl, methyl, 1,2,3-trihydroxypropyl, phosphate, and 2-carboxy-2-hydroxyethyl groups.

Advantageous Effects of Invention

The method for producing a polysaccharide of the present invention achieves a high yield of polysaccharide per unit enzyme.

DESCRIPTION OF EMBODIMENTS

The present invention provides a method for producing a polysaccharide, including allowing polysaccharide synthase (B) to act on ribonucleoside diphosphate-monosaccharide (A) shown below to produce a polysaccharide, wherein in 10 to 100% of the duration in which (B) acts on (A), the concentration of ribonucleoside diphosphate in a reaction solution is lower than 100 times a inhibitory concentration $IC_{50}$ described below against polysaccharide synthase (B).

Inhibitory concentration $IC_{50}$: a concentration of ribonucleoside diphosphate at which an enzyme activity of polysaccharide synthase (B) is reduced by half under a condition where (B) has a concentration at which (B) acts on ribonucleoside diphosphate-monosaccharide (A), wherein ribonucleoside diphosphate-monosaccharide (A) is used as a substrate and ribonucleoside diphosphate is used as an inhibitor.

Ribonucleoside diphosphate-monosaccharide (A): a sugar nucleotide in which a proton of at least one hydroxyl group of at least one monosaccharide (a) selected from the group consisting of triose (a-1), tetrose (a-2), pentose (a-3), hexose (a-4), heptose (a-5), and monosaccharide (a-6) described below is substituted with a functional group represented by any one of chemical formulae (1) to (5) below:

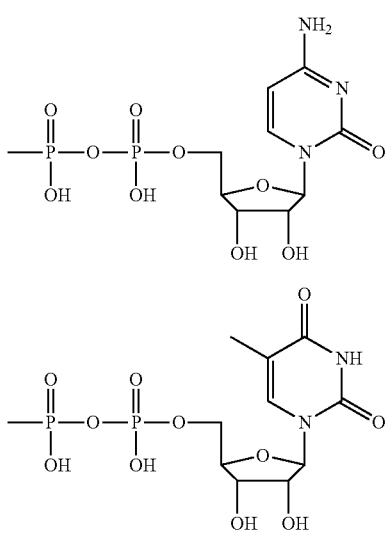

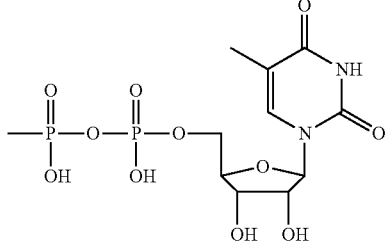

Monosaccharide (a-6): a monosaccharide selected from the group consisting of (a-1), (a-2), (a-3), (a-4), and (a-5), in which at least one member selected from the group consisting of a proton, a hydroxyl group, and a hydroxymethyl group of the monosaccharide is substituted with substituent (E) described below:

Substituent (E): at least one substituent selected from the group consisting of carboxyl, amino, N-acetylamino, sulfate, methylester, N-glycolyl, methyl, 1,2,3-trihydroxypropyl, phosphate, and 2-carboxy-2-hydroxyethyl groups.

Monosaccharide (a) includes optical isomers and stereoisomers.

Triose (a-1) is a $C_3$ monosaccharide. Specific examples thereof include dihydroxyacetone and glyceraldehyde.

Tetrose (a-2) is a $C_4$ monosaccharide. Specific examples thereof include erythrose, threose, and erythrulose.

Pentose (a-3) is a $C_5$ monosaccharide. Specific examples thereof include arabinose, xylose, ribose, xylulose, ribulose, and deoxyribose.

Hexose (a-4) is a $C_6$ monosaccharide. Specific examples thereof include glucose, mannose, galactose, fructose, sorbose, tagatose, fucose, fuculose, and rhamnose.

Heptose (a-5) is a $C_7$ monosaccharide. Specific examples thereof include sedoheptulose.

Monosaccharide (a-6) having substituent (E) includes (a-6-1) to (a-6-10) in which at least one of a proton (—H), a hydroxyl group (—OH), and a hydroxymethyl group (—CH$_2$OH) in the molecules of monosaccharides (a-1) to (a-5) is substituted with at least one substituent selected from the group consisting of carboxyl, amino, N-acetylamino, sulfate, methylester, N-glycolyl, methyl, 1,2,3-trihydroxypropyl, phosphate, and 2-carboxy-2-hydroxyethyl groups. Monosaccharide (a-6) having substituent (E) also includes (a-6-11) described below.

(a-6-1): a monosaccharide having a carboxyl group (—COOH) as a substituent, (a-6-2): a monosaccharide having an amino group (—NH$_2$) as a substituent, (a-6-3): a monosaccharide having an N-acetylamino group (—NHCOCH$_3$) as a substituent, (a-6-4): a monosaccharide having a sulfate group (—OSO$_3$H) as a substituent, (a-6-5): a monosaccharide having a methylester group (—COOCH$_3$) as a substituent, (a-6-6): a monosaccharide having an N-glycolyl group (—NHCOCH$_2$OH) as a substituent, (a-6-7): a monosaccharide having a methyl group as a substituent, (a-6-8): a monosaccharide having a 1,2,3-trihydroxypropyl group (—CHOHCHOHCH$_2$OH) as a substituent, (a-6-9): a monosaccharide having a phosphate group (—OPO$_3$H$_2$) as a substituent, (a-6-10): a monosaccharide having a 2-carboxy-2-hydroxyethyl group (—CH$_2$CHOHCOOH) as a substituent, and (a-6-11): a monosaccharide in which at least two of a proton, a hydroxyl group, and a hydroxymethyl group in the molecules of (a-1) to (a-5) are substituted with at least two types of substituents (E).

Specific examples of (a-6-1) include uronic acids such as glucuronic acid, iduronic acid, mannuronic acid, and galacturonic acid.

Specific examples of (a-6-2) include amino sugars such as glucosamine, galactosamine, and mannosamine.

Specific examples of (a-6-3) include N-acetylglucosamine, N-acetylmannosamine, and N-acetylgalactosamine.

Specific examples of (a-6-4) include galactose-3-sulfate.

Specific examples of (a-6-5) include glucose methyl ester and a methyl-esterified product of carboxylic acid in (a-6-1).

Specific examples of (a-6-11) include N-acetylmuramic acid, muramic acid, N-acetylglucosamine-4-sulfate, iduronic acid-2-sulfate, glucuronic acid-2-sulfate, N-acetylgalactosamine-4-sulfate, sialic acid, neuraminic acid, N-glycolylneuraminic acid, and N-acetylneuraminic acid.

In the case where (a-6) has at least one member (anion group) as substituent (E) selected from the group consisting of carboxyl, phosphate, 2-carboxy-2-hydroxyethyl, and sulfate groups, one or more protons of the anion group may be substituted with an alkali metal (e.g., Li, Na, or K) cation and/or alkaline earth metal (e.g., Ca) cation.

Ribonucleoside diphosphate-monosaccharide (A) includes sugar nucleotides (A-1) to (A-6) in which a proton of at least one hydroxyl group of monosaccharides (a-1) to (a-6) is substituted with anyone of chemical formulae (1) to (5) above.

Specific examples of (A-3) include uridine diphosphate-xylose.

Specific examples of (A-4) include cytidine diphosphate-glucose, guanosine diphosphate-mannose, guanosine diphosphate-fucose, adenosine diphosphate-glucose, uridine diphosphate-glucose, uridine diphosphate-galactose, and uridine diphosphate-mannose.

Specific examples of (A-6) include uridine diphosphate-glucuronic acid, uridine diphosphate-N-acetylglucosamine, uridine diphosphate-uridine diphosphate-N-acetylgalactosamine, and uridine diphosphate-iduronic acid.

In the production method of the present invention, the types of (A) may be used alone or in combination of two or more thereof. Additionally, one type of (A) may be used to produce a polysaccharide consisting of multiple chains of one type of monosaccharides. Two types of (A) may be used to produce a polysaccharide consisting of chains of two types of monosaccharides in an alternating or random pattern. Three or more types of (A) may be used to produce a polysaccharide consisting of chains of three or more types of monosaccharides in a random or regular pattern. Also, two or more types of (A) and two or more types of (B) may be used to produce several types of polysaccharides.

Polysaccharide synthase (B) is an enzyme having a polysaccharide-synthesizing activity to synthesize a polysaccharide from (A). The polysaccharide of the present invention consists of 2 to 10,000,000 of monosaccharides (a-1) to (a-6) bonded together, and includes polysaccharides having a weight average molecular weight of 200 to 1,000,000,000. It also includes a compound having a structure in which a polypeptide or lipid is bonded to a polysaccharide. It may include any compound as long as the compound has a polysaccharide moiety.

Polysaccharide synthase (B) includes hyaluronan synthase (B-1) whose target polysaccharide for synthesis is hyaluronan; chondroitin synthase (B-2) whose target polysaccharide for synthesis is chondroitin; xanthan synthase (B-3) whose target polysaccharide for synthesis is xanthan; and cellulose synthase (B-4) whose target polysaccharide for synthesis is cellulose, starch synthase (B-5), and heparin synthase (B-6). (B) also includes, in addition to (B-1) to (B-6), an enzyme having an activity to synthesize a polysaccharide from monosaccharide units.

Hyaluronan synthase (B-1) is an enzyme having a hyaluronan-synthesizing activity to synthesize hyaluronan from ribonucleoside diphosphate-glucuronic acid and ribonucleoside diphosphate-N-acetylglucosamine. Specifically, the hyaluronan-synthesizing activity is an activity to synthesize an oligosaccharide having a structure in which repeating disaccharide units consisting of glucuronic acid linked to N-acetylglucosamine by β1,3 linkages are joined by β1,4 linkages, using ribonucleoside diphosphate-glucuronic acid and ribonucleoside diphosphate-N-acetylglucosamine as sugar donors.

As for (B-1), any existing hyaluronan synthase can be used as long as it has the hyaluronan-synthesizing activity. Specific examples thereof include Class I and Class II hyaluronan synthases mentioned in Non-Patent Literature (The Journal of Biological Chemistry, 2007, Vol. 282, No. 51, pp. 36777-36781). The Class I and Class II hyaluronan synthases are categorized by homology of amino acid sequences of enzymes. Specific examples of the Class I hyaluronan synthases include hyaluronan synthases derived from *Streptococcus pyrogenes, Streptococcus equisimilis*, and algal viruses. Specific examples of the Class II hyaluronan synthases include hyaluronan synthases derived from *Pasteurella multocida*.

In the production method of the present invention, in the case where (B-1) is used as (B) to produce hyaluronan, the types of (A) to be used are preferably ribonucleoside diphosphate-glucuronic acid and ribonucleoside diphosphate-N-acetylglucosamine, and more preferably uridine diphosphate-glucuronic acid and uridine diphosphate-N-acetylglucosamine, in terms of the yield of polysaccharide per unit enzyme.

Chondroitin synthase (B-2) is an enzyme having a chondroitin-synthesizing activity to synthesize a chondroitin from ribonucleoside diphosphate-glucuronic acid and ribonucleoside diphosphate-N-acetylgalactosamine. Specifically, the chondroitin-synthesizing activity is an activity to synthesize an oligosaccharide having a structure in which repeating disaccharide units consisting of glucuronic acid linked to N-acetylgalactosamine by β1,3 linkages are joined by β1,4 linkages, using ribonucleoside diphosphate-glucuronic acid and ribonucleoside diphosphate-N-acetylgalactosamine as sugar donors. As for (B-2), any existing chondroitin synthase can be used as long as it has the chondroitin-synthesizing activity. Specific examples thereof include chondroitin synthases derived from *Streptococcus equisimilis* and chondroitin synthases derived from *Pasteurella multocida*.

In the production method of the present invention, in the case where (B-2) is used as (B) to produce chondroitin, the types of (A) to be used are preferably ribonucleoside diphosphate-glucuronic acid and ribonucleoside diphosphate-N-acetylgalactosamine, and more preferably uridine diphosphate-glucuronic acid and uridine diphosphate-N-acetylgalactosamine, in terms of the yield of polysaccharide per unit enzyme.

Xanthan synthase (B-3) is an enzyme having a xanthan-synthesizing activity to synthesize xanthan from ribonucleoside diphosphate-glucose, ribonucleoside diphosphate-mannose, and ribonucleoside diphosphate-glucuronic acid. Specifically, the xanthan-synthesizing activity is an activity to synthesize xanthan, using ribonucleoside diphosphate-glucose, ribonucleoside diphosphate-mannose, and ribonucleoside diphosphate-glucuronic acid as sugar donors. As for (B-3), any existing xanthan synthase can be used as long as it has the xanthan-synthesizing activity. Specific examples thereof include a xanthan synthase that can be produced from *Xanthomonas campestris*.

In the production method of the present invention, in the case where (B-3) is used as (B) to produce xanthan, the types of (A) to be used are preferably ribonucleoside diphosphate-glucose, ribonucleoside diphosphate-mannose, and ribonucleoside diphosphate-glucuronic acid, and more preferably uridine diphosphate-glucose, guanosine diphosphate-mannose, and uridine diphosphate-glucuronic acid, in terms of the yield of polysaccharide per unit enzyme.

Cellulose synthase (B-4) is an enzyme having a cellulose-synthesizing activity to synthesize cellulose in which ribonucleoside diphosphate-β-glucose molecules are linearly linked by glycosidic bonds. Specifically, the cellulose-synthesizing activity is an activity to form a β1,4 linkage using ribonucleoside diphosphate glucose as a sugar donor. As for (B-4), any existing cellulose synthase can be used as long as it has the cellulose-synthesizing activity. Specific examples thereof include cellulose synthase derived from acetic acid bacteria.

In the production method of the present invention, in the case where (B-4) is used as (B) to produce cellulose, the type of (A) to be used is preferably ribonucleoside diphosphate-β-glucose, and more preferably uridine diphosphate-β-glucose, in terms of the yield of polysaccharide per unit enzyme.

Starch synthase (B-5) is an enzyme having a starch-synthesizing activity to synthesize starch in which ribonucleoside diphosphate-α-glucose molecules are linearly linked by glycosidic bonds. Specifically, the starch-synthesizing activity is an activity to form a α1,6 linkage using ribonucleoside diphosphate-α-glucose as a sugar donor. As for (B-5), any existing starch synthase can be used as long as it has the starch-synthesizing activity. Specific examples thereof include a starch synthase derived from corn.

In the production method of the present invention, in the case where (B-5) is used as (B) to produce starch, the type of (A) to be used is preferably ribonucleoside diphosphate-α-glucose, and more preferably uridine diphosphate-α-glucose, in terms of the yield of polysaccharide per unit enzyme.

Heparin synthase (B-6) is an enzyme having a heparin-synthesizing activity to synthesize heparin from ribonucleoside diphosphate-glucuronic acid or ribonucleoside diphosphate-iduronic acid and ribonucleoside diphosphate-glucosamine. Specifically, the heparin-synthesizing activity is an activity to form a 1,4 linkage, using ribonucleoside diphosphate-glucuronic acid (β-D-) or ribonucleoside diphosphate-iduronic acid (α-L-) and ribonucleoside diphosphate-glucosamine (D-glucosamine) as sugar donors. As for (B-6), any existing heparin synthase can be used as long as it has the heparin-synthesizing activity. Specific examples thereof include a heparin synthase derived from human.

In the production method of the present invention, in the case where (B-6) is used a (B) to produce heparin, the types of (A) to be used are preferably ribonucleoside diphosphate-glucuronic acid or ribonucleoside diphosphate-iduronic acid and ribonucleoside diphosphate-glucosamine, and more preferably uridine diphosphate-glucuronic acid or uridine diphosphate-iduronic acid and uridine diphosphate-glucosamine, in terms of the yield of polysaccharide per unit enzyme.

Sugar nucleotide (A) and polysaccharide synthase (B) above are suitably selected depending on the type of polysaccharide to be produced.

In the production method of the present invention, the concentration of ribonucleoside diphosphate in a reaction solution is lower than 100 times an inhibitory concentration $IC_{50}$ described below against polysaccharide synthase (B). Inhibitory concentration $IC_{50}$: refers to a concentration of ribonucleoside diphosphate at which an enzyme activity of polysaccharide synthase (B) is reduced by half under a condition where (B) has a concentration at which (B) acts on ribonucleoside diphosphate-monosaccharide (A), wherein ribonucleoside diphosphate-monosaccharide (A) is used as a substrate and ribonucleoside diphosphate is used as an inhibitor.

The inhibitory concentration $IC_{50}$ can be determined by the following measurement under a condition where a reaction solution for measurement is adjusted such that the concentration of (B), temperature, and pH are the same as those of a reaction solution used in production process, which are given at any point from the beginning to the end of the step of allowing (B) to act on (A).

<Measurement Method of the Inhibitory Concentration $IC_{50}$>

An enzyme reaction solution (I) containing specific amounts of polysaccharide synthase (B), ribonucleoside diphosphate-monosaccharide (A), ribonucleoside diphosphate, pH adjuster (K), and water is prepared, which is adjusted to a specific temperature and a specific pH.

The temperature of the enzyme reaction solution (I) is adjusted to be the same as that of a reaction solution used in the production process, which is given at any point from the beginning to the end of the step of allowing (B) to act on (A) during the production process.

The pH of the enzyme reaction solution (I) is adjusted to be the same as that of a reaction solution used in the production process, which is given at any point from the beginning to the end of the step of allowing (B) to act on (A) during the production process.

The molar concentration of (B) in the enzyme reaction solution (I) is adjusted to be the same as that of (B) of a reaction solution used in the production process, which is given at any point from the beginning to end of the step of allowing (B) to act on (A).

As for the ribonucleoside diphosphate content (molar concentration) in the enzyme reaction solution (I), a total of five or more types of the enzyme reaction solutions (I) are prepared including: the enzyme reaction solution (I) in which the concentration of ribonucleoside diphosphate is 0 M, and four or more types of the enzyme reaction solutions (I) that differ in the concentration of ribonucleoside diphosphate, ranging from 0 M to a value at which the activity of polysaccharide synthase (B) is 0 (i.e., the production of polysaccharide cannot be observed). In the case where an inhibition constant Ki of ribonucleoside diphosphate for a polysaccharide synthase similar to (B) to be used for measurement is known, a total of five or more types of the enzyme reaction solutions may be prepared including: one in which the concentration of ribonucleoside diphosphate is 0 M; two or more types in which the concentration of ribonucleoside diphosphate is lower than the Ki for the similar synthase and higher than 0 M; and two or more types in which the concentration of ribonucleoside diphosphate is in the range from not lower than Ki to not higher than 10 times the Ki.

As for the amount of ribonucleoside diphosphate-monosaccharide (A) in the enzyme reaction solution (I), a concentration at which changes in the peak area over time are observable may be selected. In the case where the Michaelis constant Km for a polysaccharide synthase similar to (B) to be used for measurement is known, a concentration may be selected in the range from not lower than the Km to not higher than 5 times the Km.

In terms of the easy handling and stability of the enzyme, pH adjuster (K) to be used in the enzyme reaction solution (I) is preferably phosphate, borate, Good buffer such as HEPES buffer, or MES buffer. The amount (molar concentration) of (K) in the enzyme reaction solution (I) is 10 to 500 mM.

A portion (e.g., 100 µL) of the enzyme reaction solution (I) prepared is extracted immediately after preparation and at certain time intervals (e.g., 5 min). The extracted portions are heated at 100° C. for 1 minute to stop the enzyme reaction. Using liquid chromatography (hereinafter abbreviated as HPLC), the amount of polysaccharide in each extracted reaction solution is quantitated. An initial enzyme reaction velocity v (M/s) is calculated from the difference $\Delta P$ ($\Delta P = P_h - P_0$) in peak areas and a calibration curve based on the peak areas of the polysaccharide, wherein $P_0$ is the peak area immediately after preparation of the enzyme reaction solution (I), and $P_h$ is the peak area after h hour(s) from preparation.

The above measurement is performed in a similar manner using other enzyme reaction solutions (I) each having a different concentration of ribonucleoside diphosphate so as to separately calculate the initial enzyme reaction velocity v.

The concentration of ribonucleoside diphosphate of each enzyme reaction solution (I) is plotted on the horizontal axis (x-axis), and the relative activity is plotted on the vertical axis (y-axis), assuming that the initial enzyme reaction velocity v is 100(%) when the concentration of ribonucleoside diphosphate is 0. The plots are connected with a straight line, and the concentration of ribonucleoside diphosphate when y=50(%) is regarded as the inhibitory concentration $IC_{50}$.

In the present invention, the concentration of ribonucleoside diphosphate in the reaction solution is preferably lower than 100 times the inhibitory concentration $IC_{50}$ and more preferably not more than 10 times the inhibitory concentration $IC_{50}$ in terms of efficient polysaccharide production.

The higher the concentration of ribonucleoside diphosphate, the more the activity of polysaccharide synthase (B) is inhibited. The presence of ribonucleoside diphosphate concentrated to 100 times the $IC_{50}$ will inhibit the polysaccharide synthase activity to 1/100. Thus, the presence of ribonucleoside diphosphate concentrated to 100 times the $IC_{50}$ will require addition of 100 times more polysaccharide synthase to the reaction mixture. Contaminating enzymes in the polysaccharide synthase solution will also be incorporated into the reaction mixture at the same time. In other words, in the case where the polysaccharide synthase has a purity of 99% and the reaction mixture contains ribonucleoside diphosphate concentrated to 100 times the $IC_{50}$, adding to the reaction mixture the polysaccharide synthase in an amount 100 times more than the amount that is added to the reaction mixture containing no ribonucleoside diphosphate will result in the inclusion of contaminating enzymes in an amount comparable to the amount of the polysaccharide synthase that is added to the reaction mixture containing no ribonucleoside diphosphate. This will create undesirable reactions caused by the contaminating enzymes. This problem can be solved by increasing the purity of the polysaccharide synthase. However, it is very difficult to achieve a purity of 99% or higher in the case of purification of enzymes on the industrial scale. Thus, the concentration of ribonucleoside diphosphate must be lower than 100 times the inhibitory concentration $IC_{50}$.

In the case where several types of (B) are used, the inhibitory concentration $IC_{50}$ against each (B) is measured. Preferably, the concentration of ribonucleoside diphosphate is in the above range of the inhibitory concentration $IC_{50}$ against at least one (B).

In the step of allowing (B) to act on (A), the period in which the concentration of ribonucleoside diphosphate is in the above range is 10 to 100% of the duration in which (B) acts on (A). In terms of reaction efficiency, the period is preferably 30 to 100%, more preferably 50 to 100%, particularly preferably 80 to 100%, and most preferably 90 to 100%.

In the conventional production method that uses polysaccharide synthase (B), the activity of (B) is inhibited by ribonucleoside diphosphate produced as a by-product, which imposes problems such as low polysaccharide production efficiency, low yield, and a requirement for a large amount of (B). In contrast, in the present invention, because the concentration of ribonucleoside diphosphate in the reaction solution is in the above range while (B) acts on (A), ribonucleoside diphosphate is less likely to inhibit the activity of (B) and thus the production efficiency is high, compared to the conventional production method. Further, because the activity of (B) is less likely to be inhibited, the yield of polysaccharide per unit enzyme is high, and there is no need of using a large amount of (B).

In the production method of the present invention, the concentration of ribonucleoside diphosphate is adjusted within the above range by the following methods (i) to (iii), for example:

(i) a method for converting ribonucleoside diphosphate to compound (c) (described below) using ribonucleoside diphosphate conversion enzyme (D);
(ii) a method for adsorbing ribonucleoside diphosphate in the reaction solution using a silica gel carrier or the like; and
(iii) a method for converting ribonucleoside diphosphate to another compound through a chemical reaction.

In the method (ii), in addition to the silica gel carrier, any other carriers such as activated carbon and zeolite can be used as long as they can adsorb ribonucleoside diphosphate.

In the method (iii), any commonly known chemical reaction can be used as long as it can convert ribonucleoside diphosphate to another compound.

In the present invention, the method (i) is preferred for adjusting the concentration of ribonucleoside diphosphate within the above range in terms of a high substrate specificity of the reaction and reduced problems associated with, for example, degradation of a substrate (ribonucleoside diphosphate-monosaccharide (A)).

Specifically, the method (i) for converting ribonucleoside diphosphate to compound (C) using ribonucleoside diphosphate conversion enzyme (D) includes a method described below.

A method for producing a polysaccharide, including allowing polysaccharide synthase (B) to act on ribonucleoside diphosphate-monosaccharide (A) to produce a polysaccharide, wherein (B) is allowed to act in the presence of ribonucleoside diphosphate conversion enzyme (D) having an activity to convert ribonucleoside diphosphate to compound (C) described below. Compound (C): at least one compound selected from the group consisting of purine base or pyrimidine base (C-1), ribonucleoside (C-2), ribonucleoside monophosphate (C-3), ribonucleoside triphosphate (C-4), polyribonucleotide (C-5), deoxyribonucleoside diphosphate (C-6), and ribonucleoside diphosphate-monosaccharide (C-7).

Examples of (C-1) include purine bases (e.g., adenine and guanine) and pyrimidine bases (e.g., thymine, cytosine, and uracil).

(C-2) is a compound in which the base of (C-1) is bonded to a monosaccharide. Specific examples thereof include uridine, adenosine, ribothymidine, cytidine, and guanosine.

(C-3) is a monophosphorylated product of (C-2). Specific examples thereof include uridylic acid (uridine 5'-phosphate), adenosine monophosphate (adenosine 5'-phosphate), ribothymidylic acid (ribothymidine 5'-phosphate), cytidine monophosphate (cytidine 5'-phosphate), and guanosine monophosphate (guanosine 5'-phosphate).

(C-4) is a triphosphorylated product of (C-2). Specific examples thereof include uridine triphosphate (uridine 5'-triphosphate), adenosine triphosphate (adenosine 5'-triphosphate), ribothymidine-triphosphate (ribothymidine 5'-triphosphate), cytidine triphosphate (cytidine 5'-triphosphate), and guanosine triphosphate (guanosine 5'-triphosphate).

(C-5) is a polymer formed from polymerization of (C-3) by phosphodiester bonds. Specific examples thereof include polyuridylic acid, polyadenylic acid, polythymidylic acid, polycytidylic acid, and polyguanylic acid.

(C-6) is a compound in which ribose in the molecule of ribonucleoside diphosphate is converted to 2-deoxyribose. Specific examples thereof include deoxyuridine diphosphate, deoxyadenosine diphosphate, deoxyguanosine diphosphate, deoxycytidine diphosphate, and thymidine diphosphate.

(C-7) includes ribonucleoside diphosphate-monosaccharide (A) described above.

Ribonucleoside diphosphate conversion enzyme (D) includes (D1) to (D7) described below.

(D1): an enzyme having an activity to convert ribonucleoside diphosphate to a purine base or pyrimidine base,
(D2): an enzyme having an activity to convert ribonucleoside diphosphate to ribonucleoside,
(D3): an enzyme having an activity to convert ribonucleoside diphosphate to ribonucleoside monophosphate,
(D4): an enzyme having an activity to convert ribonucleoside diphosphate to ribonucleoside triphosphate,
(D5): an enzyme having an activity to convert ribonucleoside diphosphate to polyribonucleotide,
(D6): an enzyme having an activity to convert ribonucleoside diphosphate to deoxyribonucleoside diphosphate, and
(D7): an enzyme having an activity to convert ribonucleoside diphosphate to ribonucleoside diphosphate-monosaccharide.

(D2) is an enzyme that catalyzes the hydrolysis of a phosphate ester bond between sugar and phosphate in ribonucleotide to produce nucleoside and phosphate. Specific examples of (D2) include apyrase.

(D3) is an enzyme that catalyzes the hydrolysis of phosphoric diester such as ribonucleoside diphosphate to produce phosphoric monoester. Specific examples of (D3) include adenosine diphosphate (ADP)-specific phosphofructokinase and nucleotidase.

(D4) is an enzyme that catalyzes the transfer of a phosphate group from a phosphate-containing compound to ribonucleoside diphosphate to produce ribonucleoside triphosphate. Specific examples of (D4) include nucleoside diphosphate kinase, polyphosphate kinase, arginine kinase, pyruvate kinase, carbamate kinase, phosphoglycerate kinase, and phosphocreatine kinase.

(D4) includes uridine triphosphate synthase (D4-1). Ribonucleoside diphosphate acted on by (D4-1) is uridine diphosphate. (D4-1) is an enzyme that catalyzes the synthesis of uridine triphosphate.

Nucleoside diphosphate kinase is an enzyme that catalyzes the transfer of a phosphate group from nucleoside triphosphate to nucleoside diphosphate. Specific examples of nucleoside diphosphate kinase include those derived from living organisms (e.g., animals such as human, bovine, and rat; plants such as *Arabidopsis* and rice; and microorganisms such as *Escherichia, Saccharomyces, Bacillus*, and *Thermus*); products of chemical modification of those derived from living organisms (e.g., products that are chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Polyphosphate kinase is an enzyme having an activity to produce, from ribonucleoside diphosphate and polyphosphoric acid, ribonucleoside triphosphate and polyphosphoric acid having one smaller degree of polymerization than the above polyphosphoric acid. Specific examples of polyphosphate kinase include those derived from living organisms (e.g., plants such as *Nicotiana*; and microorganisms such as *Escherichia, Corynebacterium, Pseudomonas*, and *Thermus*); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Arginine kinase is an enzyme having an activity to produce ribonucleoside triphosphate and L-arginine from ribonucleoside diphosphate and ω-phosphono-L-arginine. Specific examples of arginine kinase include those derived from living organisms (e.g., animals such as *Drosophilidae, Decapoda*, and *Siphonaptera*; plants such as *Sabellida*; and microorganisms such as *Bacillus*); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Pyruvate kinase is an enzyme having an activity to produce ribonucleoside triphosphate and pyruvic acid from ribonucleoside diphosphate and phosphoenolpyruvic acid. Specific examples of pyruvate kinase include those derived from living organisms (e.g., animals such as human, bovine, and rat; plants such as *Arabidopsis* and *Ricinus communis*; and microorganisms such as *Escherichia* and *Saccharomyces*); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Carbamate kinase is an enzyme having an activity to produce ribonucleoside triphosphate, carbon dioxide, and ammonia from carbamoyl phosphate and ribonucleoside diphosphate. Specific examples of carbamate kinase include those derived from living organisms (e.g., animals such as rat; and microorganisms such as *Pyrococcus* and *Lactobacillus*); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Phosphoglycerate kinase is an enzyme having an activity to produce ribonucleoside triphosphate and glycerate 3-phosphate from 1,3-Bisphosphoglycerate and ribonucleoside diphosphate. Specific examples of phosphoglycerate kinase include those derived from living organisms (e.g., animals such as rat; and microorganisms such as *Saccharomyces*); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

Phosphocreatine kinase is an enzyme having an activity to produce ribonucleoside triphosphate and creatine from phosphocreatine and ribonucleoside diphosphate. Specific examples of phosphocreatine kinase include those derived from living organisms (e.g., animals such as rat); products of chemical modification of those derived from living organisms (e.g., products chemically modified by the action of at least one member selected from the group consisting of a carbodiimide compound, succinic anhydride, iodoacetic acid, and an imidazole compound); and products of genetic modification of those derived from living organisms (e.g., products genetically modified in accordance with the method of Smith et al. (The Journal of Biochemistry, 1998, Vol. 253, No. 18, pp. 6551-6560)).

The types of (D4) may be used alone or in combination of two or more thereof.

Among the types of (D4), arginine kinase, nucleoside diphosphate kinase, polyphosphate kinase, and carbamate kinase are preferred in terms of a high level of ribonucleoside triphosphate-synthesizing activity.

When allowing (D4) to act, if necessary, phosphate-containing compound (F) that donates a phosphate group to ribonucleoside diphosphate may be used. (F) is a compound containing a phosphate group, and is preferably a compound that can donate a phosphate group to ribonucleoside diphosphate, in terms of substrate specificity of (D4). Examples of (F) include triaminophosphine oxide, phosphorylated amino acids (e.g., ω-phosphono-L-arginine), polyphosphoric acid, phosphoenolpyruvic acid and salts thereof (e.g., lithium salt, sodium salt, and potassium salt), carbamoyl phosphate, 1,3-Bisphosphoglycerate, phosphocreatine, and nucleoside triphosphate (e.g., guanosine triphosphate and adenosine triphosphate).

In the case where phosphate-containing compound (F) is used, examples of preferred combinations of (D4) with (F) include: a combination of nucleoside diphosphate kinase with nucleoside triphosphate; a combination of polyphosphate kinase with polyphosphoric acid; a combination of arginine kinase with ω-phosphono-L-arginine; a combination of pyruvate kinase with phosphoenolpyruvic acid and a salt thereof; a combination of carbamate kinase with carbamoyl phosphate; a combination of phosphoglycerate kinase with 1,3-Bisphosphoglycerate; a combination of phosphoglycerate kinase with 1,3-Bisphosphoglycerate; and a combination of phosphocreatine kinase with phosphocreatine.

In the case where ribonucleoside diphosphate conversion enzyme (D) is uridine triphosphate synthase (D4-1), compound (C) is uridine triphosphate, and ribonucleoside diphosphate-monosaccharide (A) is uridine diphosphate-monosaccharide, it is preferred that a Michaelis constant Km described below is lower than 100 times the inhibitory concentration $IC_{50}$ described below.

Michaelis constant Km: a Michaelis constant of the reaction to synthesize uridine triphosphate in the presence of phosphate-containing compound (F), using uridine diphosphate as a substrate and (D4-1) as an enzyme.

Inhibitory concentration $IC_{50}$: a concentration of uridine diphosphate at which an enzyme activity of polysaccharide synthase (B) is reduced by half under a condition where (B) has a concentration at which (B) acts on uridine diphosphate-monosaccharide, wherein uridine diphosphate-monosaccharide is used as a substrate and uridine diphosphate is used as an inhibitor.

The Michaelis constant Km can be determined through determination of the dependence of the initial enzyme reaction velocity on the substrate concentration in accordance with the method reported by Agarwal et al. (described in Methods of Enzymology, 1978, Vol. 51, pp. 483-491). (D4-1) in a purified form is used for the measurement of the Michaelis constant Km. The inhibitory concentration $IC_{50}$ is determined by the method described above.

(D5) is an enzyme that catalyzes the reaction that converts ribonucleoside diphosphate such as ribonucleoside diphosphate to a copolymer of ribonucleoside monophosphate (e.g., polyribonucleotide) and inorganic phosphoric acid. Specific examples of (D5) include polyribonucleotide nucleotidyltransferase.

(D6) is an enzyme that catalyzes the reaction that reduces ribonucleotide such as ribonucleoside diphosphate into deoxyribonucleotide (e.g., deoxyuridine diphosphate). Specific examples of (D6) include ribonucleoside diphosphoreductase.

In the case where (D6) is used as ribonucleoside diphosphate conversion enzyme (D), reducing agent (d6) must be used. An electron transport protein can be used as (d6). Examples thereof include reduced thioredoxin.

(D7) is an enzyme that catalyzes the reaction that synthesizes nucleotide sugar (ribonucleoside diphosphate-monosaccharide) from ribonucleoside diphosphate such as ribonucleoside diphosphate and sugar or sugar phosphate. Specific examples of (D7) include sucrose synthase and N-acyl neuraminate cytidylyltransferase.

In the case where (D7) is used as ribonucleoside diphosphate conversion enzyme (D), sugar (d7-1) or sugar phosphate (d7-2) must be used as raw material (d7) of nucleotide sugar.

(d7-1) includes monosaccharides, disaccharides, and oligosaccharides. Specific examples thereof include sucrose.

(d7-2) is a compound in which one phosphoric acid is linked to one hydroxyl group of a monosaccharide. Examples thereof include glucuronic acid 1-phosphate (e.g., 1-phospho-α-D-glucuronate) and N-acetylglucosamine-1-phosphate (e.g., N-acetyl-D-glucosamine-1-phosphate).

Ribonucleoside diphosphate-monosaccharide synthesized by (D7) may be the same as or different from (A) that is a raw material used in the production method of the present invention. (A) will be synthesized in the case where sugar (d7-1) or sugar phosphate (d7-2) is a compound in which one phosphoric acid is linked to one hydroxyl group of monosaccharide (a) described above for ribonucleoside diphosphate-monosaccharide (A) used as a raw material of the production method of the present invention.

Preferred among the types of ribonucleoside diphosphate conversion enzyme (D) are (D2), (D3), (D4), (D5), and (D7); more preferred is (D4); and particularly preferred is (D4-1) in terms of efficient polysaccharide production and easy industrialization.

The types of (D) may be used alone or in combination of two or more thereof.

In the present invention, in the case where ribonucleoside diphosphate conversion enzyme (D) is used, an enzyme activity ratio ($Y_1$) calculated from the following formula (1) using enzyme activity $Vmax_1$ and enzyme activity $Vmax_2$ described below is preferably not lower than 0.1 in terms of efficient polysaccharide production and efficient use of the substrate (ribonucleoside diphosphate-monosaccharide (A)).

$$\text{Enzyme activity ratio } (Y_1) = Vmax_1 / Vmax_2 \quad (1)$$

Enzyme activity $Vmax_1$: the enzyme activity of ribonucleoside diphosphate conversion enzyme (D) on ribonucleoside diphosphate.

Enzyme activity $Vmax_2$: the enzyme activity of ribonucleoside diphosphate conversion enzyme (D) on ribonucleoside diphosphate-monosaccharide (A).

The enzyme activity $Vmax_1$ and $Vmax_2$ can be measured by the below-described enzyme activity Vmax measurement method.

<Enzyme Activity Vmax Measurement Method>

An enzyme reaction solution (II) containing specific amounts of substrate (ribonucleoside diphosphate or uridine diphosphate-monosaccharide (A)), enzyme (polysaccharide synthase (B) or ribonucleoside diphosphate conversion enzyme (D)), pH adjuster (K), and water is prepared, which is adjusted to a specific temperature and a specific pH.

Phosphate-containing compound (F) is added, if necessary, to the enzyme reaction solution (II) if the enzyme to be used is (D4). Reducing agent (d6) is added if the enzyme is (D6), and raw material (d7) of nucleotide sugar is added if the enzyme is (D7).

After preparation of the enzyme reaction solution (II), it is allowed to stand for enzyme reaction for 1 minute to 100 hours. Next, the amount (X) of the reaction product obtained from the reaction is measured to determine the initial enzyme reaction velocity v. Likewise, the initial enzyme reaction velocity v is determined, using the enzyme reaction solution (II) having a different substrate concentration. A Lineweaver-Burk plot is generated from the above-obtained initial enzyme reaction velocity v and substrate concentration, and the enzyme activity Vmax is determined therefrom.

Herein, the enzyme reaction solution (II) may have any temperature in the range of 0° C. to 100° C. as long as it is a temperature at which the enzyme activity is maintained without being deactivated and which can be maintained at a constant level during the period from preparation of the enzyme reaction solution (II) to the end of the measurement.

The enzyme reaction solution (II) may have any pH as long as it is in the pH range of 3 to 12. In the case where an optimum pH of polysaccharide synthase (B) described below is known, the pH of the enzyme reaction solution (II) is preferably the optimum pH.

In terms of easy handling and enzyme stability, pH adjuster (K) to be used in the enzyme reaction solution (II) is preferably a Good buffer such as HEPES buffer or MES buffer. The concentration (molar concentration) of pH adjuster (K) in the enzyme reaction solution (II) is 25 to 500 mM.

The enzyme concentration (molar concentration) in the enzyme reaction solution (II) is suitably selected depending on the type of (D). Specifically, a concentration at which a linear function is plotted is selected, with the vertical axis plotting the amount (X) of the reaction product (described later) and the horizontal axis plotting the time h.

In the case where the enzyme is (D4) and phosphate-containing compound (F) is added to the enzyme reaction solution (II), the concentration (molar concentration) of (F) therein is 1 nM to 10 M. The concentration of (F) is adjusted to a level so that the reaction velocity remains the same even when the concentration of (F) is doubled or halved.

In the case where the enzyme is (D6), the concentration (molar concentration) of reducing agent (d6) in the enzyme reaction solution (II) is 1 nM to 10 M. The concentration of (d6) is adjusted to a level so that the reaction velocity remains the same even when the concentration of (d6) is doubled or halved.

In the case where the enzyme is (D7), the concentration (molar concentration) of raw material (d7) of nucleotide sugar in the enzyme reaction solution (II) is 1 nM to 10 M. The concentration of (d7) is adjusted to a level so that the reaction velocity remains the same even when the concentration of (d7) is doubled or halved.

As for the substrate concentration (molar concentration) in the enzyme reaction solution (II), at least three different concentrations may be selected in the range from the minimum substrate concentration to the maximum substrate concentration in which the amount (X) of the reaction product can be observed over time.

If the reaction time is too short, the amount (X) of the reaction product cannot be accurately measured. On the other hand, if the reaction time is too long, unfortunately, the enzyme will be deactivated or the substrate will be exhausted. Thus, the time taken until a linear function is plotted is regarded as the reaction time, with the vertical axis plotting the amount (X) of the reaction product and the horizontal axis plotting the time.

The amount (X) of the reaction product is determined through analysis with HPLC under appropriate conditions in order to measure the amount of the reaction product in a quantitative manner. Herein, the reaction product is a product produced by conversion of the substrate by the activity of polysaccharide synthase (B) or ribonucleoside diphosphate conversion enzyme (D).

The enzyme activity Vmax (M/s) is determined using Lineweaver-Burk plot derived from Michaelis-Menten kinetics. In the Lineweaver-Burk plot, the horizontal axis (x-axis) plots the reciprocal (1/[S]) of each substrate concentration, and the vertical axis (y-axis) plots the reciprocal (1/v) of the initial enzyme reaction velocity at each substrate concentration. The intersection of an approximate straight line of the plots with the y-axis is the reciprocal (1/Vmax) of the enzyme activity Vmax.

In the above measurement, the result determined using ribonucleoside diphosphate conversion enzyme (D) as an enzyme and ribonucleoside diphosphate as a substrate represents $Vmax_1$, and the result determined using ribonucleoside diphosphate conversion enzyme (D) as an enzyme and ribonucleoside diphosphate-monosaccharide (A) as a substrate represents $Vmax_2$. In the case where two or more types of ribonucleoside diphosphate-monosaccharide (A) are used, $Vmax_2$ is determined for each ribonucleoside diphosphate-monosaccharide (A). The enzyme activity ratio ($Y_1$) is also determined for each type from formula (1) using each $Vmax_2$. The enzyme activity ratio ($Y_1$) of each type is preferably not lower than 0.1, in terms of efficient polysaccharide production and efficient use of the substrate (ribonucleoside diphosphate-monosaccharide (A)).

In the polysaccharide production, in the case where two or more types of (D) are used, the enzyme activity ratio ($Y_1$) is determined for each (D). Preferably, the enzyme activity ratio ($Y_1$) of at least one type of (D) is not lower than 0.1, and more preferably, the enzyme activity ratio ($Y_1$) of each (D) is not lower than 0.1, in terms of efficient polysaccharide production and efficient use of the substrate (ribonucleoside diphosphate-monosaccharide (A)).

<Measurement Method of Optimum pH for Polysaccharide Synthase (B)>

Enzyme reaction solutions (III) each containing specific amounts of ribonucleoside diphosphate-monosaccharide (A), polysaccharide synthase (B), pH adjuster (K), and water are prepared. The pH of each enzyme reaction solution (III) varies in the range of 3 to 12. Next, each enzyme reaction solution (III) is allowed to stand for reaction for 1 minute to 100 hours. Further, the amount of polysaccharide produced in each enzyme reaction solution (III) is measured. The pH at which the yield of polysaccharide reaches the maximum value is regarded as the optimum pH, with the vertical axis plotting the yield of polysaccharide and the horizontal axis plotting the pH.

Each enzyme reaction solution (III) may have any temperature in the range of 0° C. to 100° C. as long as it is a temperature at which the activity of polysaccharide synthase (B) is maintained without being deactivated and the absorbance can be measured, and which can be maintained at a constant level during the period from preparation of the enzyme reaction solution (III) to the end of the measurement.

In terms of the easy handling and stability, pH adjuster (K) to be used in the enzyme reaction solution (III) is preferably a Good buffer such as HEPES buffer or MES buffer. The concentration (molar concentration) of pH adjuster (K) in the enzyme reaction solution (III) is 25 to 500 mM.

The concentration (molar concentration) of ribonucleoside diphosphate-monosaccharide (A) in the enzyme reaction solution (III) is 10 mM. In the case where several types of (A) are used, the concentration (molar concentration) of each type is 10 mM. As for the type(s) of (A), one or more that are suitable as targets for the action of (B) are selected (for example, when (B) is (B-1), ribonucleoside diphosphate-glucuronic acid and ribonucleoside diphosphate-N-acetylglucosamine are used as (A)).

The concentration (U/L) of polysaccharide synthase (B) in the enzyme reaction solution (III) is 0.001 to 10,000 U/L. (Note that 1 U represents the amount of enzyme to produce ribonucleoside diphosphate from 1 μmol of ribonucleoside diphosphate-sugar per minute.)

If the reaction time is too short, the yield of polysaccharide cannot be accurately measured. On the other hand, if the reaction time is too long, unfortunately, the enzyme will be deactivated or the substrate will be exhausted. Thus, the time taken until a linear function is plotted during which the yield of polysaccharide can be accurately measured is regarded as the reaction time, with the vertical axis plotting the yield of polysaccharide and the horizontal axis plotting the time.

The yield of polysaccharide can be measured using ribonucleoside diphosphate-monosaccharide labeled with a radioactive isotope. For example, a polysaccharide is synthesized using ribonucleoside diphosphate-monosaccharide (A) (e.g., ribonucleoside diphosphate-glucuronic acid) in which a monosaccharide (e.g., glucuronic acid) is labeled with $^{14}C$; the polysaccharide is separated from the unreacted substrate (ribonucleoside diphosphate-monosaccharide (A)) by paper chromatography using filter paper; and the yield of polysaccharide is measured.

Likewise, the yield of polysaccharide is measured for each of the enzyme reaction solutions (III) having different pH values (pH of 3 to 12).

The pH at which the amount of polysaccharide synthesis is the maximum is the optimum pH, with the vertical axis plotting the amount of polysaccharide synthesis and the horizontal axis plotting the pH.

Further, in the present invention, an enzyme activity ratio $(Y_2)$ calculated from the following formula (2) using the above-described enzyme activity $Vmax_1$ and the below-described enzyme activity $Vmax_3$ is preferably not lower than 0.1.

$$\text{Enzyme activity ratio } (Y_2) = Vmax_1/Vmax_3 \quad (2)$$

Enzyme activity $Vmax_3$: the enzyme activity of polysaccharide synthase (B) on ribonucleoside diphosphate-monosaccharide (A).

The enzyme activity $Vmax_3$ can be measured with the enzyme activity Vmax measurement method, using polysaccharide synthase (B) as an enzyme and ribonucleoside diphosphate-monosaccharide (A) as a substrate.

In the case where two or more types of ribonucleoside diphosphate-monosaccharide (A) are used, $Vmax_3$ is determined for each type of ribonucleoside diphosphate-monosaccharide (A). The enzyme activity ratio $(Y_2)$ is also determined for each type from formula (2) using each $Vmax_3$. The enzyme activity ratio $(Y_2)$ of each type is preferably not lower than 0.1, in terms of efficient polysaccharide production and efficient use of the substrate (ribonucleoside diphosphate-monosaccharide (A)).

In the polysaccharide production, in the case where two or more types of (B) and/or two or more types of (D) are used, the enzyme activity ratio $(Y_2)$ is determined for each (B) and each (D). In terms of efficient polysaccharide production and efficient use of the substrate (ribonucleoside diphosphate-monosaccharide (A)), preferably, the enzyme activity ratio $(Y_2)$ of at least one type of (B) and (D) is not lower than 0.1, and more preferably, the enzyme activity ratio $(Y_2)$ of each type of (B) and (D) is not lower than 0.1.

The production method of the present invention may be similar to a conventional method for producing a polysaccharide, including allowing polysaccharide synthase (B) to act on ribonucleoside diphosphate-monosaccharide (A), as long as the concentration of ribonucleoside diphosphate in a reaction solution is lower than 100 times the inhibitory concentration $IC_{50}$ against polysaccharide synthase (B). Examples include a method for producing a polysaccharide using ribonucleoside diphosphate conversion enzyme (D), the method including steps (a) to (c) described below. In the description below, the step of allowing (B) to act on (A) includes steps (a) and (b), and the step of allowing (B) to act in the presence of ribonucleoside diphosphate conversion enzyme (D) includes steps (a) and (b). Step (a): a reaction solution (Z) is prepared by mixing specific amounts of ribonucleoside diphosphate-monosaccharide (A), polysaccharide synthase (B), ribonucleoside diphosphate conversion enzyme (D), and solvent (H), which is then adjusted to a specific temperature and a specific pH. In this step, stirring may be involved, if necessary.

The reaction solution (Z) may also be prepared by mixing ribonucleoside diphosphate-monosaccharide (A) and solvent (H), adjusting the temperature and pH of the mixture, and subsequently adding (B) and (D) thereto. (B) and (D) may be directly added or may be first diluted with solvent (H).

If (D) is (D4), phosphate-containing compound (F) may be added to the reaction solution (Z). If (D) is (D6), reducing agent (d6) is added. If (D) is (D7), raw material (d7) of nucleotide sugar is added.

The reaction solution (Z) may further contain lipid (L), sugar (M), and oligosaccharide (N).

Step (b): polysaccharide synthase (B) is allowed to act on ribonucleoside diphosphate-monosaccharide (A) for a predetermined period of time while the temperature of reaction solution (Z) is adjusted. In this step, stirring may be involved, if necessary.

Step (c): The produced polysaccharide is purified. Examples of polysaccharide purification methods include a method in which a solvent such as an alcohol ($C_1$-$C_{10}$ alcohol) in an adequate amount is added to cause precipitation, and a method in which a solution is exchanged using a membrane (specific examples include a ceramic membrane).

The amount (molar concentration) of ribonucleoside diphosphate-monosaccharide (A) in the reaction solution (Z) is preferably 0.1 mM to 2 M in terms of efficient polysaccharide production and efficient action of polysaccharide synthase (B). In the case where the reaction solution (Z) contains several types of (A), the amount (molar concentration) of each type is preferably 0.1 mM to 2 M.

The amount (wt %) of polysaccharide synthase (B) in the reaction solution (Z) is preferably 0.1 to 100,000 U/L in terms of efficient polysaccharide production and efficient action of polysaccharide synthase (B).

Herein, 1 U represents the amount of enzyme that converts 1 μmol of the substrate (ribonucleoside diphosphate-monosaccharide (A)) to polysaccharide per minute. For example, in the case where (B) is (B-1), and uridine diphosphate-glucuronic acid and uridine diphosphate-N-acetylglucosamine are used as (A), 1 U represents the amount of enzyme that converts a total of 1 μmol of uridine diphosphate-glucuronic acid and uridine diphosphate-N-acetylglucosamine to polysaccharide per minute.

The amount (U/L) of ribonucleoside diphosphate conversion enzyme (D) in the reaction solution (Z) is preferably 0.1 to 100,000 U/L in terms of efficient polysaccharide production and efficient action of polysaccharide synthase (B).

Note that 1 U represents the amount of enzyme that converts 1 μmol of the substrate (ribonucleoside diphosphate) to compound (C) per minute.

The amount (molar concentration) of each of phosphate-containing compound (F), reducing agent (d6), and raw material (d7) of nucleotide sugar in the reaction solution (Z) is preferably 0.01 nM to 10 M in terms of efficient polysaccharide production and efficient action of polysaccharide synthase (B).

Examples of solvent (H) include water and pH adjuster (K)-containing water. As such a pH adjuster, an existing pH adjuster can be used, and examples thereof include borate buffer, phosphate buffer, acetate buffer, Tris buffer, HEPES buffer, sulfuric acid, hydrochloric acid, citric acid, lactic acid, pyruvic acid, formic acid, sodium chloride, potassium chloride, monoethanolamine, and diethanolamine.

The temperature of the reaction solution (Z) is preferably 0° C. to 100° C. in terms of the stability of (B) and (D) and reaction velocity.

The pH of the reaction solution (Z) is preferably 3 to 12 in terms of optimized reaction conditions. Moreover, the pH of the reaction solution (Z) is preferably the optimum pH of (B) in terms of efficient polysaccharide production.

In steps (a) and (b), lipid (L), sugar (M), and oligosaccharide (N) may be used in addition to uridine diphosphate-monosaccharide (A), polysaccharide synthase (B), ribonucleoside diphosphate conversion enzyme (D), phosphate-containing compound (F), reducing agent (d6), and raw material (d7) of nucleotide sugar in terms of the stability and activation of the enzyme.

Examples of lipid (L) include cardiolipin and oleic acid.

Examples of sugar (M) include glycerin.

Examples of oligosaccharide (N) include oligo hyaluronic acid.

The amount (wt %) of lipid (L) in the reaction solution (Z) is preferably 0 to 1 in terms of the stability and activation of the enzyme.

The amount (wt %) of sugar (M) in the reaction solution (Z) is preferably 0 to 30 in terms of the stability and activation of the enzyme.

The amount (wt %) of oligosaccharide (N) in the reaction solution (Z) is preferably 0 to 1 in terms of the stability and activation of the enzyme.

In step (b), the duration of action of polysaccharide synthase (B) varies depending on the factors such as the activity of polysaccharide synthase (B), temperature of reaction solution (Z), and quantitative ratio between polysaccharide synthase (B) and ribonucleoside diphosphate-monosaccharide (A). The reaction time can be shortened by adjusting the temperature of the reaction solution (Z) to a temperature at which the activity of polysaccharide synthase (B) is high and the reaction velocity is thus high. The greater the amount of polysaccharide synthase (B) relative to ribonucleoside diphosphate-monosaccharide (A) in the reaction solution (Z), the faster the reaction and the shorter the reaction time.

In the production method of the present invention, the concentration of ribonucleoside diphosphate is set to be lower than 100 times the inhibitory concentration $IC_{50}$. Thereby, the activity of polysaccharide synthase (B) is less likely to be inhibited, the action of (B) on ribonucleoside diphosphate-monosaccharide (A) per unit enzyme is highly efficient, and polysaccharide can thus be efficiently produced. Further, in the production method of the present invention, the reaction solution is free from impurities such as chondroitin sulfate, glycosaminoglycan sulfate, and microorganisms, and is thus easily purified. Furthermore, compared to the conventional production method that uses a polysaccharide synthase, the production cost of polysaccharide is low because the activity of polysaccharide synthase (B) is less likely to be inhibited and a large amount of polysaccharide synthase (B) is thus unnecessary.

In the production method of the present invention, the following conditions are preferred: the polysaccharide is hyaluronan; the types of ribonucleoside diphosphate-monosaccharide (A) are uridine diphosphate-glucuronic acid and uridine diphosphate-N-acetylglucosamine; polysaccharide synthase (B) is hyaluronan synthase (B-1); compound (C) is uridine triphosphate; and ribonucleoside diphosphate conversion enzyme (D) is uridine triphosphate synthase (D4-1). In this case, more preferably, the reaction solution (Z) further contains phosphate-containing compound (F), 1-phospho-glucuronic acid, and uridine triphosphate-monosaccharide-1-phosphate uridylyltransferase (G), in terms of efficient production of hyaluronan (i.e., polysaccharide).

1-Phospho-glucuronate is a product in which a hydroxyl group at position 1 of the glucuronic acid is phosphorylated with phosphoric acid.

Uridine triphosphate-monosaccharide-1-phosphate uridylyltransferase (G) is not particularly limited as long as it is an enzyme having an activity to produce uridine diphosphate-glucuronic acid from uridine triphosphate and 1-phospho-glucuronic acid. Examples thereof include animal uridine triphosphate-monosaccharide-1-phosphate uridylyltransferase (G-1) originated from animals; plant uridine triphosphate-monosaccharide-1-phosphate uridylyltransferase (G-2) originated from plants; microorganism uridine triphosphate-monosaccharide-1-phosphate uridylyltransferase (G-3) originated from microorganisms; variant (G-4) obtained by chemical modification of (G-1) to (G-3); and variant (G-5) obtained by genetic modification of (G-1) to (G-3).

Examples of animal uridine triphosphate-monosaccharide-1-phosphate uridylyltransferase (G-1) include those derived from porcine.

Examples of plant uridine triphosphate-monosaccharide-1-phosphate uridylyltransferase (G-2) include those derived from *Arabidopsis*, *Pisum sativum*, and *Hordeum vulgare* L.

Examples of microorganism uridine triphosphate-monosaccharide-1-phosphate uridylyltransferase (G-3) include those derived from *Thermus*.

Examples of chemically-modified uridine triphosphate-monosaccharide-1-phosphate uridylyltransferase (G-4) include those obtained by chemical modification of the above uridine triphosphate-monosaccharide-1-phosphate uridylyltransferase by the action of a carbodiimide compound, succinic anhydride, iodoacetic acid, an imidazole compound, or the like.

Examples of genetically modified uridine triphosphate-monosaccharide-1-phosphate uridylyltransferase (G-5) include those obtained by genetic modification of the above uridine triphosphate-monosaccharide-1-phosphate uridylyltransferase and subsequent replacement of amino acids in accordance with the method of Smith et al. (The Journal of Biochemistry, 1998, Vol. 253, No. 18, pp. 6551-6560).

Preferred among the types of uridine triphosphate-monosaccharide-1-phosphate uridylyltransferase (G) is (G-2), and more preferred is nucleoside-2-phosphate kinase derived from *Arabidopsis*, in terms of a high level of the activity to synthesize uridine diphosphate-glucuronic acid.

As for uridine triphosphate-monosaccharide-1-phosphate uridylyltransferase (G), two or more types thereof may be used.

The amount (molar concentration) of 1-phospho-glucuronic acid in the reaction solution (Z) is preferably 0.0001 mM to 1 M, and more preferably 0.01 mM to 100 mM in terms of promoting conversion to uridine diphosphate-glucuronic acid.

The amount (U/mL) of uridine triphosphate-monosaccharide-1-phosphate uridylyltransferase (G) in the reaction solution (Z) is preferably 0.00001 U/mL to 10,000 U/mL, and more preferably 0.001 U/mL to 1,000 U/mL in terms of improved conversion efficiency of uridine diphosphate-glucuronic acid.

Note that 1 U represents the amount of enzyme to convert 1 μmol of uridine triphosphate and 1 μmol of 1-phospho-glucuronic acid to uridine diphosphate-glucuronic acid per minute.

The production method of the present invention is preferably a method in which steps (1) to (3) described below are simultaneously performed in terms of efficient hyaluronan production, in the case where hyaluronan (i.e., polysaccharide) is produced in the reaction solution (Z) containing phosphate-containing compound (F), 1-phospho-glucuronic acid, and uridine triphosphate-monosaccharide-1-phosphate uridylyltransferase (G), using uridine diphosphate-glucuronic acid and uridine diphosphate-N-acetylglucosamine as ribonucleoside diphosphate-monosaccharide (A), hyaluronan synthase (B-1) as polysaccharide synthase (B), uridine triphosphate as compound (C), and uridine triphosphate synthase (D4-1) as ribonucleoside diphosphate conversion enzyme (D).

Step (1): a step of producing hyaluronan and uridine diphosphate by allowing hyaluronan synthase (B-1) to act on uridine diphosphate-glucuronic acid and uridine diphosphate-N-acetylglucosamine;

Step (2): a step of producing uridine triphosphate by allowing uridine triphosphate synthase (D4-1) to act on uridine diphosphate and phosphate-containing compound (F); and Step (3): a step of producing uridine diphosphate-glucuronic acid by allowing uridine triphosphate-monosaccharide-1-phosphate uridylyltransferase (G) to act on uridine triphosphate and 1-phospho-glucuronic acid.

In the case of the method in which steps (1) to (3) described above are simultaneously performed, a Michaelis constant Km described below is preferably lower than 100 times the inhibitory concentration $IC_{50}$ described below.

Michaelis constant Km: a Michaelis constant of the reaction to synthesize uridine triphosphate in the presence of phosphate-containing compound (F), using uridine diphosphate as a substrate and (D4-1) as an enzyme.

Inhibitory concentration $IC_{50}$: a concentration of uridine diphosphate at which an enzyme activity of (B-1) is reduced by half under a condition where (B-1) has a concentration at which (B-1) acts on uridine diphosphate-glucuronic acid and uridine diphosphate-N-acetylglucosamine, wherein uridine diphosphate-glucuronic acid and uridine diphosphate-N-acetylglucosamine are used as substrates and uridine diphosphate is used as an inhibitor.

The Michaelis constant Km can be determined through determination of the dependence of the initial enzyme reaction velocity on the substrate concentration in accordance with the method reported by Agarwal et al. (described in Methods of Enzymology, 1978, Vol. 51, pp. 483-491). (D4-1) in a purified form is used for the measurement of the Michaelis constant Km.

No particular limitation is imposed to the hyaluronan production method in which steps (1) to (3) described above are simultaneously performed as long as the reactions in step (1) to (3) are carried out in the same reaction solution. Specific examples include a method in which phosphate-containing compound (F), uridine triphosphate synthase (D4-1), 1-phospho-glucuronic acid, uridine triphosphate-monosaccharide-1-phosphate uridylyltransferase (G), uridine diphosphate-glucuronic acid, uridine diphosphate-N-acetylglucosamine, hyaluronan synthase (B-1), and solvent (H) are blended to prepare a reaction solution (Z'), and hyaluronan is produced therein. The reaction solution (Z') may contain pyrophosphate degrading enzyme, lipid (L), sugar (M), and oligosaccharide (N). The concentration of each component in the reaction solution (Z), reaction conditions, and the like are similar to those for the production method that includes steps (a) to (c) described above.

In the production method in which steps (1) to (3) described above are simultaneously performed, there is a case where a pyrophosphoric acid is produced as a by-product and inhibits the activities of enzymes ((B-1), (D4-1), and (G)). Thus, it is preferred to use the pyrophosphate degrading enzyme in the production method of the present invention because it degrades pyrophosphoric acid and thus can alleviate the pyrophosphoric acid-induced inhibition of the enzyme activities of (B-1), (D4-1) and (G).

Examples of the pyrophosphate degrading enzyme include enzymes classified in EC 3.1.3 and EC 3.6.1. Specific examples thereof include alkaline phosphatase, apyrase, phytase, and diphosphatase.

Among these, diphosphatase is preferred as the pyrophosphate degrading enzyme because it is less likely to dissolve the reaction products (uridine triphosphate and hyaluronan).

The pyrophosphate degrading enzyme content (U/mL) in the reaction solution (Z) is preferably 0.00001 to 100 in terms of degradation of pyrophosphoric acid without degrading the reaction products (uridine triphosphate, uridine diphosphate-glucuronic acid, and hyaluronan).

In the pyrophosphate degrading enzyme, 1 U represents the amount of enzyme to degrade 1 μmol of pyrophosphoric acid per minute.

The method for producing a polysaccharide of the present invention enables highly efficient polysaccharide production. The polysaccharide produced by the production method of the present invention can be used not only in cosmetic products, quasi drugs, medicinal products, and medical devices, but also in other products such as food.

EXAMPLES

The present invention is described in further detail below with reference to examples and comparative examples, but the present invention is not limited thereto.

Preparation 1

A gene encoding the amino acid sequence of SEQ ID NO: 1 derived from *Streptococcus equisimilis* was fused with a FLAG tag, and this gene was incorporated into a plasmid (pKK223-3). The plasmid was then transformed into *Escherichia coli* (E. coliSURE), followed by culturing at 30° C. for 5 hours. Expression was induced when the turbidity of the culture medium reached 0.5 (turbidimeter: "UV-1700" available from Shimadzu Corporation, 1 mL of quartz cell). Subsequently, *Escherichia coli* was recovered using a centrifuge ("5922" available from KUBOTA Corporation (hereinafter the same), 4° C., 6000×g, 15 min). The recovered

*Escherichia coli* was resuspended in buffer solution A (100 mM phosphate buffer (pH of 7.0) containing 100 mM sodium chloride, 10 mM magnesium chloride, 10 mM dodecylmaltoside, and 5 mM oleic acid), followed by ultrasonic fragmentation (130 W, 10 min) and then purification on an anti-FLAG antibody column. Thereby, hyaluronan synthase aqueous solution (B-1) was obtained.

<Measurement of the Specific Activity of Hyaluronan Synthase Aqueous Solution (B-1)>

Reaction solution (1) was prepared by adding 10 μL of hyaluronan synthase aqueous solution (B-1) obtained in Preparation 1 to 1 mL of aqueous solution S (50 mM phosphate buffer (pH of 7.0) containing 1 mM uridine diphosphate-glucuronic acid (labeled radioactive radioactivity of 300 mCi/mmol), 1 mM uridine diphosphate-N-acetylglucosamine, 100 mM sodium chloride, 10 mM magnesium chloride, 10 mM dodecylmaltoside, and 5 mM oleic acid). Four such reaction solutions (1) were prepared and allowed to react at 30° C. for 5 minutes, 10 minutes, 15 minutes, and 20 minutes, respectively. Hyaluronan was separated from the unreacted substrate by paper chromatography (developing solvent containing 1 M ammonium acetate (pH of 5.5) and ethanol at a 7:13 ratio, hereinafter the same) using filter paper (Whatman No. 3 MM, hereinafter the same), and then the origin was cut out and immersed in a liquid scintillation cocktail. The radioactive isotope was then measured using a liquid scintillation counter. The amount of hyaluronan synthesis was calculated from the amount of uptake of $^{14}$C-labeled glucuronic acid. The results were 1.6 mg after 5 minutes, 2.9 mg after 10 minutes, 4.2 mg after 15 minutes, and 5.5 mg after 20 minutes. The specific activity of hyaluronan synthase aqueous solution (B-1) was calculated from the relationship between the amount of hyaluronan synthesis and the reaction time. The result was 0.15 U/μL.

<Measurement of the Inhibitory Concentration $IC_{50}$ Against Hyaluronan Synthase>

Hyaluronan synthase aqueous solution (B-1) obtained in Preparation 1 was dissolved to a concentration of 1.5 U/mL in 940 μL of aqueous solution 1 (50 mM phosphate buffer (pH of 7.5, 25° C.) containing 5 mM magnesium chloride and 0.05 mM sodium uridine diphosphate) in a 1.5 mL-tube. The tube was allowed to stand at 40° C. for 20 minutes in a constant temperature water bath. To the tube was added 50 μL of temperature-adjusted (40° C.) substrate solution [1-1] (a solution obtained by dissolving uridine diphosphate-glucuronic acid sodium salt and uridine diphosphate-N-acetylglucosamine both to a concentration of 20 mM in buffer solution B (50 mM phosphate buffer, pH of 7.5, 25° C.)). Thereby, enzyme reaction solution (I-1) was obtained. A portion (100 μL) of (I-1) was extracted immediately after preparation and at 5-minute intervals. Each extracted portion was heated at 100° C. for 2 minutes to stop the enzyme reaction. The solution in which the enzyme reaction was stopped was centrifuged using a centrifuge (4° C., 12,000×g, 10 min) to precipitate impurities. The supernatant (80 μL) was analyzed by HPLC under the following conditions, and the peak areas of hyaluronan were recorded.

<HPLC Measurement Conditions>

Hereinafter, HPLC measurement was performed under the same conditions.
Device: ACQUITY UPLC system
Column: Shodex OHpak SB-806M HQ
Mobile phase: 0.1 M NaNO$_3$
Flow rate: 1.0 mL/min
Detector: ACQUITY UPLC RID detector
Temperature: 40° C.

Solutions were prepared by changing the sodium uridine diphosphate concentration in aqueous solution 1 to the following concentrations: 0 mM (aqueous solution 2), 0.15 mM (aqueous solution 3), 3 mM (aqueous solution 4), 1 mM (aqueous solution 5), and 3 mM (aqueous solution 6)). Enzyme reaction solutions (I-2) to (I-6) were prepared in a similar manner, except that aqueous solutions 2 to 6 were used in place of aqueous solution 1. The peak areas of hyaluronan were recorded for enzyme reaction solutions (I-2) to (I-6) in a similar manner as in enzyme reaction solution (I-1).

Sodium hyaluronate ("Hyalose" available from Funakoshi Corporation; molecular mass: 175 kDa) was dissolved in buffer solution B to prepare hyaluronan standard solutions (1) to (4) having concentrations of 0.001 μg/mL, 0.01 μg/mL, 0.1 μg/mL, and 5 μg/mL, respectively. Then, (1) to (4) were analyzed by HPLC, and the peak areas of hyaluronan were recorded accordingly. Each hyaluronan concentration (μg) was plotted on the horizontal axis (x-axis) and each peak area P was plotted on the vertical axis (y-axis) to calculate the slope "k" of the straight line.

In each (I-1) to (I-6), the peak area of uridine triphosphate immediately after preparation of the solution was assigned $P_0$, and the peak area after "m" minute(s) was assigned $P_h$. Then, for each solution, the initial enzyme reaction velocity v (μg/s) was calculated from the difference ΔP (ΔP=$P_h$−$P_0$) in the peak areas and the slope of the straight line, using formula (1) below:

$$v = \Delta P / (k \times m \times 60) \tag{1}$$

The initial enzyme reaction velocities measured using enzyme reaction solutions (I-1) and (I-3) to (I-6) were converted through calculation into relative values (%), with the initial enzyme reaction velocity v measured using enzyme reaction solution (I-2) as 100%. Using the calculated relative values, each uridine diphosphate concentration [S] was plotted on the horizontal axis (x-axis), and the relative values of the initial enzyme reaction velocities v measured using enzyme reaction solutions (I-1) to (I-6) were plotted on the vertical axis (y-axis). The uridine diphosphate concentration at the intersection of the approximate curve of the plots with the straight line y=50(%) was considered to be the inhibitory concentration $IC_{50}$. The inhibitory concentration $IC_{50}$ was 0.11 mM.

Further, the inhibitory concentration $IC_{50}$ was measured in a similar manner as described above, except that the amount of hyaluronan synthase aqueous solution (B-1) was changed from 1.5 U/mL to 45 U/mL. The inhibitory concentration $IC_{50}$ was 0.11 mM.

<Measurement of the Enzyme Activity $Vmax_3$ and the Enzyme Activity Ratio ($Y_2$) of Hyaluronan Synthase>

The enzyme activity $Vmax_3$ for each of uridine diphosphate-glucuronic acid and uridine diphosphate-N-acetylglucosamine was determined in a similar manner as in "Measurement of the enzyme activities $Vmax_1$ and $Vmax_2$, and the enzyme activity ratio ($Y_1$) of sucrose synthase" described below, except that "hyaluronan synthase aqueous solution (B-1)" was used in place of "sucrose synthase aqueous solution (D7-1)", "uridine diphosphate-glucuronic acid and uridine diphosphate-N-acetylglucosamine" were used as substrates in place of "uridine diphosphate", and "sucrose" was not used.

Then, the enzyme activity ratio ($Y_2$) was determined from the enzyme activity $Vmax_3$ determined above and the enzyme activity $Vmax_1$ determined for each of solutions (D2-1), (D3-1), (D4-1-1) to (4-1-3), (D5-1), (D6-1), and (D7-1) described later. The enzyme activity ratio ($Y_2$) of each type was not lower than 0.1.

Preparation 2

Sucrose synthase aqueous solution (D7-1) was obtained in a similar manner as in Preparation 1, except that a "gene encoding the amino acid sequence of SEQ ID NO: 2 derived from *Vicia faba*" was used in place of the "gene encoding the amino acid sequence of SEQ ID NO: 1 derived from *Streptococcus equisimilis*".

<Measurement of the Specific Activity of Sucrose Synthase Aqueous Solution (D7-1)>

Reaction solution (2) was prepared by adding 10 μL of 1 M sucrose aqueous solution and 10 μL of sucrose synthase aqueous solution (D7-1) to 1 mL of aqueous solution R (50 mM phosphate buffer (pH of 7.0) containing 100 mM sodium chloride, 10 mM magnesium chloride, and 1 mM uridine diphosphate). Three such reaction solutions (2) were prepared and allowed to react at 30° C. for 5 minutes, 10 minutes, and 15 minutes, respectively. As for the amount of compound (C-7) as the reaction product (uridine diphosphate-glucose), the reaction product was developed on TLC (PEI-Cellulose plate available from Sigma-Aldrich Corporation, hereinafter the same) (developing solvent: an aqueous solution containing 1 M LiCl and 1 M formic acid, hereinafter the same), and detected with a UV light (260 nm). The specific activity of sucrose synthase aqueous solution (D7-1) was calculated to be 0.3 U/μL from the relationship between the yield of compound (C-7) and the reaction time.

<Measurement of the Enzyme Activities $Vmax_1$ and $Vmax_2$, and the Enzyme Activity Ratio ($Y_1$) of Sucrose Synthase>

Enzyme reaction solution (II-1) was prepared by adding the following to 1 mL of aqueous solution P (50 mM phosphate buffer (pH of 7.0) containing 100 mM sodium chloride and 10 mM magnesium chloride): a substrate (uridine diphosphate) to a concentration of 0.5 mM in the solution, sucrose (available from Wako Pure Chemical Industries, Ltd.) to a concentration of 100 mM in the solution, and 1 μL of sucrose synthase aqueous solution (D7-1). Then, the reaction was initiated. Enzyme reaction solution (II-1) was allowed to stand at 30° C. for enzyme reaction for 30 minutes while measuring the amount of the reaction product (uridine diphosphate-glucose) using HPLC at 5-minute intervals, and the initial enzyme reaction velocity v was calculated. The initial enzyme reaction velocity v was also calculated in a similar manner as described above for enzyme reaction solutions (II-2), (II-3), and (II-4), which were prepared by changing the uridine diphosphate concentration of enzyme reaction solution (II-1) to 0.3 mM, 0.1 mM, and 0.05 mM, respectively.

A Lineweaver-Burk plot was constructed, with the horizontal axis (x-axis) plotting the reciprocal (1/[S]) of the substrate (uridine diphosphate) concentration in each of enzyme reaction solutions (II-1) to (II-4), and the vertical axis (y-axis) plotting the reciprocal (1/v) of the initial enzyme reaction velocity at each substrate concentration. The reciprocal ($1/Vmax_1$) of the enzyme activity $Vmax_1$ was determined from the intersection of an approximate straight line of the plots with the y-axis.

$Vmax_2$ was determined in a similar manner as described above, except that "uridine diphosphate-glucuronic acid" was used as a substrate in place of "uridine diphosphate". The enzyme activity ratio ($Y_1$) was calculated to be not lower than 10 from the determined $Vmax_1$ and $Vmax_2$.

Further, $Vmax_2$ was determined in a similar manner as described above, except that "uridine diphosphate-N-acetylglucosamine" was used as a substrate in place of "uridine diphosphate". The enzyme activity ratio ($Y_1$) was calculated to be not lower than 10 from the determined $Vmax_1$ and $Vmax_2$.

Preparation 3

Ribonucleotide diphosphate reductase aqueous solution (D6-1) was obtained in a similar manner as in Preparation 1, except that a "gene encoding the amino acid sequence of SEQ ID NO: 3 derived from *Corynebacterium glutamicus*" was used in place of the "gene encoding the amino acid sequence of SEQ ID NO: 1 derived from *Streptococcus equisimilis*".

<Measurement of the Specific Activity of Ribonucleotide Diphosphate Reductase Aqueous Solution (D6-1)>

Reaction solution (3) was prepared by adding 0.1 mg of reduced thioredoxin and 10 μL of ribonucleotide diphosphate reductase aqueous solution (D6-1) to 1 mL of aqueous solution R. Three such reaction solutions (3) were prepared and allowed to react at 30° C. for 5 minutes, 10 minutes, and 15 minutes, respectively. As for the amount of compound (C-6) as the reaction product (deoxyuridine diphosphate), the reaction product was developed on TLC and detected with a UV light (260 nm). The specific activity of ribonucleotide diphosphate reductase aqueous solution (D6-1) was calculated to be 0.3 U/μL from the relationship between the yield of compound (C-6) and the reaction time.

<Measurement of the Enzyme Activities $Vmax_1$ and $Vmax_2$, and the Enzyme Activity Ratio ($Y_1$) of Ribonucleotide Diphosphate Reductase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "ribonucleotide diphosphate reductase aqueous solution (D6-1)" was used in place of "sucrose synthase aqueous solution (D7-1)", and "reduced thioredoxin" was used in place of "sucrose".

Further, $Vmax_2$ was determined in a similar manner as described above, except that "uridine diphosphate-glucuronic acid" and "uridine diphosphate-N-acetylglucosamine" were used as substrates in place of "uridine diphosphate". The enzyme activity ratio ($Y_1$) of each type was calculated to be not lower than 10 from the determined $Vmax_1$ and $Vmax_2$.

Preparation 4

Pyruvate kinase aqueous solution (D4-1-1) was obtained in a similar manner as in Preparation 1, except that a "gene encoding the amino acid sequence of SEQ ID NO: 4 derived from *Escherichia coli*" was used in place of the "gene encoding the amino acid sequence of SEQ ID NO: 1 derived from *Streptococcus equisimilis*".

<Measurement of the Specific Activity of Pyruvate Kinase Aqueous Solution (D4-1-1)>

Reaction solution (4) was prepared by adding 10 μL of 1 M monopotassium phosphoenolpyruvate aqueous solution (available from Wako Pure Chemical Industries, Ltd.) and 10 μL of pyruvate kinase aqueous solution (D4-1-1) to 1 mL of aqueous solution R. Three such reaction solutions (4) were prepared and allowed to react at 30° C. for 5 minutes, 10 minutes, and 15 minutes, respectively. For the amount of compound (C-4) as the reaction product (uridine triphosphate), the reaction product was developed on TLC and detected with a UV light (260 nm). The specific activity of pyruvate kinase aqueous solution (D4-1-1) was calculated to be 0.3 U/μL from the relationship between the yield of compound (C-4) and the reaction time.

<Measurement of the Enzyme Activities $Vmax_1$ and $Vmax_2$, and the Enzyme Activity Ratio ($Y_1$) of Pyruvate Kinase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "pyruvate kinase aqueous solution (D4-1-1)" was used in place of "sucrose synthase aqueous solution (D7-1)", and "monopotassium phosphoenolpyruvate" was used in place of "sucrose".

Further, "uridine diphosphate-glucuronic acid", "uridine diphosphate-N-acetylglucosamine", "uridine diphosphate-N-acetylgalactosamine", "uridine diphosphate-glucose", "uridine diphosphate-mannose", and "uridine diphosphate-glucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

Preparation 5

Nucleotidase aqueous solution (D3-1) was obtained in a similar manner as in Preparation 1, except that a "gene encoding the amino acid sequence of SEQ ID NO: 5 derived from *Escherichia coli*" was used in place of the "gene encoding the amino acid sequence of SEQ ID NO: 1 derived from *Streptococcus equisimilis*".

<Measurement of the Specific Activity of Nucleotidase Aqueous Solution (D3-1)>

Reaction solution (5) was prepared by adding 10 μL of nucleotidase aqueous solution (D3-1) to 1 mL of aqueous solution R. Three such reaction solutions (5) were prepared and allowed to react at 30° C. for 5 minutes, 10 minutes, and 15 minutes, respectively. For the amount of compound (C-3) as the reaction product (uridine monophosphate), the reaction product was developed on TLC and detected with a UV light (260 nm). The specific activity of nucleotidase aqueous solution (D3-1) was calculated to be 0.3 U/μL from the relationship between the yield of compound (C-3) and the reaction time.

<Measurement of the Enzyme Activities $Vmax_1$ and $Vmax_2$, and the Enzyme Activity Ratio ($Y_1$) of Nucleotidase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "nucleotidase aqueous solution (D3-1)" was used in place of "sucrose synthase aqueous solution (D7-1)", and "sucrose" was not used.

Further, "uridine diphosphate-glucuronic acid" and "uridine diphosphate-N-acetylglucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

Preparation 6

Polyribonucleotide nucleotidyltransferase aqueous solution (D5-1) was obtained in a similar manner as in Preparation 1, except that a "gene encoding the amino acid sequence of SEQ ID NO: 6 derived from *Escherichia coli*" was used in place of the "gene encoding the amino acid sequence of SEQ ID NO: 1 derived from *Streptococcus equisimilis*".

<Measurement of the Specific Activity of Polyribonucleotide Nucleotidyltransferase Aqueous Solution (D5-1)>

Reaction solution (6) was prepared by adding 1 mg of polyuridine (product name "polyuridylic acid potassium salt" available from Sigma-Aldrich Corporation) and 10 μL of polyribonucleotide nucleotidyltransferase aqueous solution (D5-1) to 1 mL of aqueous solution R. Three such reaction solutions (6) were prepared and allowed to react at 30° C. for 5 minutes, 10 minutes, and 15 minutes, respectively. For the amount of compound (C-5) as the reaction product (polyuridylic acid), the reaction product was developed on TLC and detected with a UV light (260 nm). The specific activity of polyribonucleotide nucleotidyltransferase aqueous solution (D5-1) was calculated to be 0.3 U/μL from the relationship between the yield of compound (C-5) and the reaction time.

<Measurement of the Enzyme Activities $Vmax_1$ and $Vmax_2$, and the Enzyme Activity Ratio ($Y_1$) of Polyribonucleotide Nucleotidyltransferase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "polyribonucleotide nucleotidyltransferase aqueous solution (D5-1)" was used in place of "sucrose synthase aqueous solution (D7-1)", and "sucrose" was not used.

Further, "uridine diphosphate-glucuronic acid" and "uridine diphosphate-N-acetylglucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

Preparation 7

Apyrase aqueous solution (D2-1) was obtained in a similar manner as in Preparation 1, except that a "gene encoding the amino acid sequence of SEQ ID NO: 7 derived from *xenopus*" was used in place of the "gene encoding the amino acid sequence of SEQ ID NO: 1 derived from *Streptococcus equisimilis*".

<Measurement of the Specific Activity of Apyrase Aqueous Solution (D2-1)>

Reaction solution (7) was prepared by adding 10 μL of apyrase aqueous solution (D2-1) to 1 mL of aqueous solution R. Three such reaction solutions (7) were prepared and allowed to react at 30° C. for 5 minutes, 10 minutes, and 15 minutes, respectively. For the amount of compound (C-2) as the reaction product (uridine), the reaction product was developed on TLC and detected with a UV light (260 nm). The specific activity of apyrase aqueous solution (D2-1) was calculated to be 0.3 U/μL from the relationship between the yield of compound (C-2) and the reaction time.

<Measurement of the Enzyme Activities $Vmax_1$ and $Vmax_2$, and the Enzyme Activity Ratio ($Y_1$) of Apyrase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "apyrase aqueous solution (D2-1)" was used in place of "sucrose synthase aqueous solution (D7-1)", and "sucrose" was not used.

Further, "uridine diphosphate-glucuronic acid" and "uridine diphosphate-N-acetylglucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

Preparation 8

Nucleoside diphosphate kinase aqueous solution (D4-1-2) was obtained in a similar manner as in Preparation 1, except that a "gene encoding the amino acid sequence of SEQ ID NO: 8 derived from rat pancreas" was used in place of the "gene encoding the amino acid sequence of SEQ ID NO: 1 derived from *Streptococcus equisimilis*".

<Measurement of the Specific Activity of Nucleoside Diphosphate Kinase Aqueous Solution (D4-1-2)>

Reaction solution (8) was prepared by adding 5 mM adenosine triphosphate (available from Sigma-Aldrich Corporation) to 1 mL of aqueous solution R and then adding 10 μL of nucleoside diphosphate kinase aqueous solution (D4-1-2) to the mixture. Three such reaction solutions (8) were prepared and allowed to react at 30° C. for 5 minutes, 10 minutes, and 15 minutes, respectively. For the amount of compound (C-4) as the reaction product (uridine triphosphate), the reaction product was developed on TLC and detected with a UV light (260 nm). The specific activity of nucleoside diphosphate kinase aqueous solution (D4-1-2) was calculated to be 0.3 U/μL from the relationship between the yield of compound (C-4) and the reaction time.

<Measurement of the Enzyme Activities $Vmax_1$ and $Vmax_2$, and the Enzyme Activity Ratio ($Y_1$) of Nucleoside Diphosphate Kinase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "nucleoside diphosphate kinase aqueous solution (D4-1-2)" was used in place of "sucrose synthase aqueous solution (D7-1)", and "adenosine triphosphate" was used in place of "sucrose".

Further, "uridine diphosphate-glucuronic acid", "uridine diphosphate-N-acetylglucosamine", "uridine diphosphate-N-acetylgalactosamine", "uridine diphosphate-glucose", "uridine diphosphate-mannose", and "uridine diphosphate-glucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

Preparation 9

Arginine kinase aqueous solution (D4-1-3) was obtained in a similar manner as in Preparation 1, except that a "gene encoding the amino acid sequence of SEQ ID NO: 9 derived from *Toxoplasma gondii*" was used in place of the "gene encoding the amino acid sequence of SEQ ID NO: 1 derived from *Streptococcus equisimilis*".

<Measurement of the Specific Activity of Arginine Kinase Aqueous Solution (D4-1-3)>

Reaction solution (9) was prepared by adding 1 M ω-phosphono-L-arginine aqueous solution (available from Sigma-Aldrich Corporation) to 1 mL of aqueous solution R and then adding 10 μL of arginine kinase aqueous solution (D4-1-3) to the mixture. Three such reaction solutions (9) were prepared and allowed to react at 30° C. for 5 minutes, 10 minutes, and 15 minutes, respectively. For the amount of compound (C-4) as the reaction product (uridine triphosphate), the reaction product was developed on TLC and detected with a UV light (260 nm). The specific activity of arginine kinase aqueous solution (D4-1-3) was calculated to be 0.3 U/μL from the relationship between the yield of compound (C-4) and the reaction time.

<Measurement of the Enzyme Activities $Vmax_1$ and $Vmax_2$, and the Enzyme Activity Ratio ($Y_1$) of Arginine Kinase>

The enzyme activity $Vmax_1$ for uridine diphosphate was determined in a similar manner as in "Measurement of the enzyme activities $Vmax_1$ and $Vmax_2$, and the enzyme activity ratio ($Y_1$) of sucrose synthase", except that "arginine kinase aqueous solution (D4-1-3)" was used in place of "sucrose synthase aqueous solution (D7-1)", and "monopotassium phosphoenolpyruvate" was used in place of "sucrose".

Further, "uridine diphosphate-glucuronic acid", "uridine diphosphate-N-acetylglucosamine", "uridine diphosphate-N-acetylgalactosamine", "uridine diphosphate-glucose", "uridine diphosphate-mannose", and "uridine diphosphate-glucosamine" were used as substrates in place of "uridine diphosphate", and the enzyme activity $Vmax_2$ was determined for each type in a similar manner as described above. The enzyme activity ratio ($Y_1$) was also determined. The enzyme activity ratio ($Y_1$) of each type was not lower than 10.

<Measurement of the Michaelis Constant Km in the Reaction to Synthesis Uridine Triphosphate Using Nucleoside-2-Phosphate Kinase>

Ten μL of nucleoside-2-phosphate kinase aqueous solution (D4-1-2) obtained in Preparation 8 was dissolved in 890 μL of aqueous solution 7 (50 mM phosphate buffer (pH of 7.5, 25° C.) containing 5 mM magnesium chloride and 100 mM adenosine triphosphate (available from Sigma-Aldrich Corporation)) in a 1.5 mL-tube. The tube was allowed to stand at 30° C. for 3 minutes in a constant temperature water bath. To the tube was added 100 μL of temperature-adjusted (30° C.) substrate solution [2-1] (a solution obtained by dissolving sodium uridine diphosphate to a concentration of 10 mM in buffer solution B). Thereby, enzyme reaction solution (IV-2-1) was obtained. A portion (100 μL) of (IV-2-1) was extracted immediately after preparation and at 1-minute intervals. The extracted portions were heated at 100° C. for 2 minutes to stop the enzyme reaction, and centrifuged using a centrifuge (4° C., 12,000×g, 10 min) to precipitate impurities. The supernatant (80 μL) was analyzed by HPLC, and the peak areas of uridine triphosphate were recorded.

Solutions were prepared by changing the molar concentration of sodium uridine diphosphate in substrate solution [2-1] to 5 mM (substrate solution [2-2]), 2 mM (substrate solution [2-3]), 1 mM (substrate solution [2-4]), and 0.3 mM (substrate solution [2-5]). Enzyme reaction solutions (IV-2-2) to (IV-2-5) were prepared in a similar manner as enzyme reaction solution (IV-2-1), except that substrate solutions [2-2] to [2-5] were used in place of substrate solution [2-1]. The peak areas of uridine triphosphate were recorded for enzyme reaction solutions (IV-2-2) to (IV-2-5) in a similar manner for enzyme reaction solution (IV-2-1).

Sodium uridine triphosphate (available from Wako Pure Chemical Industries, Ltd.) was dissolved in buffer solution B to prepare uridine triphosphate standard solutions (M-1) to (M-4) having concentrations of 0.005 mM, 0.1 mM, 1 mM, and 5 mM, respectively. Then, a portion (80 μL) from each of (M-1) to (M-4) was analyzed by HPLC under the same conditions described above, and the peak areas of uridine triphosphate were recorded accordingly. Each uridine triphosphate concentration (mM) was plotted on the horizontal axis (x-axis), and each peak area P was plotted on the vertical axis (y-axis) to calculate the slope "k'" of the straight line.

In enzyme reaction solutions (IV-2-1) to (IV-2-5), the peak area of uridine triphosphate immediately after preparation of the solution was assigned $P_0$, and the peak area after "m'" minute (s) was assigned $P_h$. Then, for each solution, the initial enzyme reaction velocity v (mM/s) was calculated from the difference $\Delta P$ ($\Delta P = P_h - P_0$) in the peak areas and the slope "k'" of the straight line, using formula (5) below:

$$v = \Delta P/(k' \times m' \times 60) \quad (5)$$

A Hanes-Woolf plot was constructed using the calculated initial enzyme reaction velocity v, with the horizontal axis (x-axis) plotting each substrate concentration [S], and the vertical axis (y-axis) plotting the reciprocal [S]/v of the initial enzyme reaction velocity at each substrate concentration. The Michaelis constant Km was determined to be 0.25 mM from the intersection (−Km) of an approximate straight line of the plots with the x-axis.

<Measurement of the Michaelis Constant Km in the Reaction to Synthesize Uridine Triphosphate Using Pyruvate Kinase>

The Michaelis constant Km was determined in a similar manner as in "Measurement of the Michaelis constant Km in the reaction to synthesis uridine triphosphate using nucleoside-2-phosphate kinase", except that "pyruvate kinase aqueous solution (D4-1-1) obtained in Preparation 4" was used in place of "nucleoside-2-phosphate kinase aqueous solution (D4-1-2) obtained in Preparation 8", and "monopotassium phosphoenolpyruvate" was used in place of "adenosine triphosphate". The result was 6 mM.

<Measurement of the Michaelis Constant Km in the Reaction to Synthesize Uridine Triphosphate Using Arginine Kinase>

The Michaelis constant Km was determined in a similar manner as in "Measurement of the Michaelis constant Km in the reaction to synthesis uridine triphosphate using nucleoside-2-phosphate kinase", except that "arginine kinase aqueous solution (D4-1-3) obtained in Preparation 9" was used in place of "nucleoside-2-phosphate kinase aqueous solution (D4-1-1) obtained in Preparation 8", and "ω-phosphono-L-arginine" was used in place of "adenosine triphosphate". The result was 0.71 mM.

Example 1

Reaction solution (Z-1) was prepared by adding the following to 1 mL of aqueous solution S: 100 μL of 1 M sucrose aqueous solution, 10 μL of sucrose synthase aqueous solution (D7-1) obtained in Preparation 2, and 10 μL of hyaluronan synthase aqueous solution (B-1) obtained in Preparation 1; and was allowed to react at 30° C. for 2 hours. Sampling was performed during the reaction, and the uridine diphosphate concentration in the reaction solution was measured using HPLC. Table 1 shows the results.

Further, after two hours of reaction, hyaluronan was separated from the unreacted substrate by paper chromatography using filter paper, and then the origin was cut out and immersed in a liquid scintillation cocktail. The radioactive isotope was then measured using a liquid scintillation counter. The yield of hyaluronan was calculated from the amount of uptake of $^{14}$C-labeled glucuronic acid. The yield of hyaluronan was 5.1 mg.

Example 2

Hyaluronan was synthesized in a similar manner as in Example 1, except that "10 μL of ribonucleotide diphosphate reductase aqueous solution (D6-1) obtained in Preparation 3" was used in place of "10 μL of sucrose synthase aqueous solution (D7-1) obtained in Preparation 2", and "10 mg of reduced thioredoxin" was used in place of "100 μL of 1 M sucrose aqueous solution". The yield of hyaluronan was 5.3 mg. Table 1 shows the measurement results of the uridine diphosphate concentration in the reaction solution.

Example 3

Hyaluronan was synthesized in a similar manner as in Example 1, except that "10 μL of pyruvate kinase aqueous solution (D4-1-1) obtained in Preparation 4" was used in place of "10 μL of sucrose synthase aqueous solution (D7-1) obtained in Preparation 2", and "100 μL of 1 M monopotassium phosphoenolpyruvate aqueous solution" was used in place of "100 μL of 1 M sucrose aqueous solution". The yield of hyaluronan was 5.0 mg. Table 1 shows the measurement results of the uridine diphosphate concentration in the reaction solution.

Example 4

Hyaluronan was synthesized in a similar manner as in Example 1, except that "10 μL of nucleotidase aqueous solution (D3-1) obtained in Preparation 5" was used in place of "10 μL of sucrose synthase aqueous solution (D7-1) obtained in Preparation 2", and "100 μL of 1 M sucrose aqueous solution" was not used. The yield of hyaluronan was 4.8 g. Table 1 shows the measurement results of the uridine diphosphate concentration in the reaction solution.

Example 5

Hyaluronan was synthesized in a similar manner as in Example 1, except that "10 μL of polyribonucleotide nucleotidyltransferase aqueous solution (D5-1) obtained in Preparation 6" was used in place of "10 μL of sucrose synthase aqueous solution (D7-1) obtained in Preparation 2", and "100 μL of 1 M sucrose aqueous solution" was not used. The yield of hyaluronan was 5.0 mg. Table 1 shows the measurement results of the uridine diphosphate concentration in the reaction solution.

Example 6

Hyaluronan was synthesized in a similar manner as in Example 1, except that "10 μL of apyrase aqueous solution (D2-1) obtained in Preparation 7" was used in place of "10 μL of sucrose synthase aqueous solution (D7-1) obtained in Preparation 2", and "100 μL of 1 M sucrose aqueous solution" was not used. The yield of hyaluronan was 5.3 mg.

Table 1 shows the measurement results of the uridine diphosphate concentration in the reaction solution.

Preparation 10

Uridine triphosphate-monosaccharide-1-phosphate uridylyltransferase aqueous solution (G-1) was obtained in a similar manner as in Preparation 1, except that a "gene encoding the amino acid sequence of SEQ ID NO: 10 derived from *Arabidopsis*" was used in place of the "gene encoding the amino acid sequence of SEQ ID NO: 1 derived from *Streptococcus equisimilis*".

<Measurement of the Specific Activity of Uridine Triphosphate-Monosaccharide-1-Phosphate Uridylyltransferase Aqueous Solution (G-1)>

Reaction solution (10-1) was prepared by adding 10 μL of uridine triphosphate-monosaccharide-1-phosphate uridylyltransferase aqueous solution (G-1) obtained in Preparation 10 to 1 mL of aqueous solution (50 mM phosphate buffer (pH of 7.0) containing 100 mM sodium chloride, 10 mM magnesium chloride, 10 mM uridine triphosphate, and 10 mM N-acetylglucosamine-1-phosphate). Three such reaction solutions (10-1) were prepared and allowed to react at 30° C. for 5 minutes, 10 minutes, and 15 minutes, respectively. As for the quantity of the produced uridine diphosphate-N-acetylglucosamine, the product was detected with a UV light (260 nm) in HPLC. The activity of uridine triphosphate-monosaccharide-1-phosphate uridylyltransferase to produce uridine diphosphate-N-acetylglucosamine was determined from the amount of uridine diphosphate-N-acetylglucosamine production. The result was 0.1 U/mL.

The activity of uridine triphosphate-monosaccharide-1-phosphate uridylyltransferase to produce uridine diphosphate-glucuronic acid was determined in a similar manner as described above, except that an aqueous solution containing "10 mM glucuronic acid 1-phosphate" was used in place of "10 mM N-acetylglucosamine-1-phosphate" and "uridine diphosphate-glucuronic acid" was quantitated in place of "uridine diphosphate-N-acetylglucosamine". The result was 5 U/μL.

Example 7

Reaction solution (Z-7) was prepared by adding the following to 1 mL of solution (buffer solution B (pH of 7.5, 25° C.) containing 1 mM uridine diphosphate-glucuronic acid ($^{14}$C-labeled radioactive isotope-containing uridine diphosphate-glucuronic acid; radioactivity of 300 mCi/mmol), 1 mM uridine diphosphate-N-acetylglucosamine, 100 mM adenosine triphosphate, 100 mM 1-phospho-glucuronic acid, 100 mM N-acetylglucosamine-1-phosphate, and 5 mM magnesium chloride): 10 μL of hyaluronan synthase aqueous solution (B-1) obtained in Preparation 1; 5 μL of pyrophosphate degrading enzyme (available from Roche Applied Science); 5 μL of nucleoside diphosphate kinase aqueous solution (D4-1-2) obtained in Preparation 8; and 5 μL of uridine triphosphate-monosaccharide-1-phosphate uridylyltransferase aqueous solution (G-1) obtained in Preparation 10. The temperature of the resulting mixture was adjusted in a constant temperature water bath at 30° C. to allow enzyme reaction for 2 hours. Sampling was performed during the reaction, and the uridine diphosphate concentration in the reaction solution was measured using HPLC. Table 1 shows the results.

Further, after two hours of reaction, hyaluronan was separated from the unreacted substrate by paper chromatography using filter paper, and then the origin was cut out and immersed in a liquid scintillation cocktail. The radioactive isotope was then measured using a liquid scintillation counter. The yield of hyaluronan was calculated from the amount of uptake of $^{14}$C-labeled glucuronic acid. The hyaluronan production was 16 mg.

Example 8

Hyaluronan was synthesized in a similar manner as in Example 7, except that "5 μL of pyruvate kinase aqueous solution (D4-1-1) obtained in Preparation 4" and "100 mM monopotassium phosphoenolpyruvate aqueous solution" were used in place of "5 μL of nucleoside diphosphate kinase aqueous solution (D4-1-2) obtained in Preparation 8" and "100 mM adenosine triphosphate". The yield of hyaluronan was 14 mg. Table 1 shows the measurement results of the uridine diphosphate concentration in the reaction solution.

Example 9

Hyaluronan was synthesized in a similar manner as in Example 7, except that "5 μL of arginine kinase aqueous solution (D4-1-3) obtained in Preparation 9" and "100 mM ω-phosphono-L-arginine aqueous solution" were used in place of "5 μL of nucleoside diphosphate kinase aqueous solution (D4-1-2) obtained in Preparation 8" and "100 mM adenosine triphosphate". The yield of hyaluronan was 15 mg. Table 1 shows the measurement results of the uridine diphosphate concentration in the reaction solution.

Comparative Example 1

Hyaluronan was synthesized in a similar manner as in Example 1, except that "10 μL of sucrose synthase aqueous solution (D7-1) obtained in Preparation 2" and "10 μL of 1 M sucrose aqueous solution" were not used, and the amount of hyaluronan synthase (B-1) was changed from "10 μL" to "300 μL". The yield of hyaluronan was 3.0 mg. The uridine diphosphate concentration in the reaction solution was measured as in Example 1. Table 1 shows the results.

TABLE 1

| | IC$_{50}$ (mM) against polysaccharide synthase (B) used | Concentration (mM) of ribonucleoside diphosphate in reaction solution | | | | | | Yield of polysaccharide (mg) |
|---|---|---|---|---|---|---|---|---|
| | | After 10 min | After 20 min | After 40 min | After 60 min | After 90 min | After 120 min | |
| Example 1 | 0.11 | 0.01 | 0.05 | 0.1 | 0.3 | 0.3 | 0.2 | 5.1 |
| Example 2 | 0.11 | 0.01 | 0.07 | 0.2 | 0.4 | 0.3 | 0.3 | 5.3 |
| Example 3 | 0.11 | 0.004 | 0.05 | 0.1 | 0.2 | 0.3 | 0.4 | 5.0 |
| Example 4 | 0.11 | 0.02 | 0.1 | 0.4 | 0.5 | 0.5 | 0.5 | 4.8 |
| Example 5 | 0.11 | 0.03 | 0.2 | 0.4 | 0.4 | 0.3 | 0.3 | 5.0 |

TABLE 1-continued

| | IC$_{50}$ (mM) against polysaccharide synthase (B) used | Concentration (mM) of ribonucleoside diphosphate in reaction solution | | | | | | Yield of polysaccharide (mg) |
|---|---|---|---|---|---|---|---|---|
| | | After 10 min | After 20 min | After 40 min | After 60 min | After 90 min | After 120 min | |
| Example 6 | 0.11 | 0.005 | 0.04 | 0.1 | 0.2 | 0.3 | 0.4 | 5.3 |
| Example 7 | 0.11 | 0.01 | 0.01 | 0.01 | 0.01 | 0.01 | 0.02 | 16 |
| Example 8 | 0.11 | 0.02 | 0.02 | 0.03 | 0.03 | 0.03 | 0.03 | 14 |
| Example 9 | 0.11 | 0.01 | 0.01 | 0.01 | 0.02 | 0.02 | 0.03 | 15 |
| Comparative Example 1 | 0.11 | 11 | 12 | 13 | 16 | 19 | 21 | 3.0 |

Preparation 11

Chondroitin synthase aqueous solution (B-2) was obtained in a similar manner as in Preparation 1, except that a "gene encoding the amino acid sequence of SEQ ID NO: 11 derived from *Pasteurella multocida*" was used in place of the "gene encoding the amino acid sequence of SEQ ID NO: 1 derived from *Streptococcus equisimilis*".

<Measurement of the Specific Activity of Chondroitin Synthase Aqueous Solution (B-2)>

Reaction solution (11) was prepared by adding 10 μL of chondroitin synthase aqueous solution (B-2) obtained in Preparation 11 to 1 mL of aqueous solution T (50 mM phosphate buffer (pH of 7.0) containing 1 mM uridine diphosphate-glucuronic acid ($^{14}$C-labeled radioactive isotope-containing uridine diphosphate-glucuronic acid; radioactivity of 300 mCi/mmol), 1 mM uridine diphosphate-N-acetylgalactosamine, 100 mM sodium chloride, 10 mM magnesium chloride, 10 mM dodecylmaltoside, and 5 mM oleic acid). Three such reaction solutions (11) were prepared and allowed to react at 30° C. for 5 minutes, 10 minutes, and 15 minutes, respectively. Chondroitin was separated from the unreacted substrate by paper chromatography using filter paper. Subsequently, the origin was cut out and immersed in a liquid scintillation cocktail, and the radioactive isotope was then measured using a liquid scintillation counter. The yield of chondroitin was calculated from the amount of uptake of $^{14}$C-labeled glucuronic acid. The results were 1.7 μg after 5 minutes, 3.1 μg after 10 minutes, and 4.4 μg after 15 minutes. The specific activity of chondroitin synthase aqueous solution (B-2) was calculated from the relationship between the yield of chondroitin and the reaction time. The result was 0.15 U/mL.

<Measurement of the Inhibitory Concentration IC$_{50}$ Against chondroitin Synthase>

The inhibitory concentration IC$_{50}$ was measured in a similar manner as in "Measurement of the inhibitory concentration IC$_{50}$ against hyaluronan synthase", except that "chondroitin synthase aqueous solution (B-2) obtained in Preparation 11" was used in place of "hyaluronan synthase aqueous solution (B-1) obtained in Preparation 1", "substrate solution [1-2] (a solution prepared by dissolving uridine diphosphate-glucuronic acid sodium salt and uridine diphosphate-N-acetylgalactosamine both to a concentration 20 mM in buffer solution B)" was used in place of "substrate solution [1-1]", and "sodium chondroitin (available from Wako Pure Chemical Industries, Ltd.)" was used in place of "sodium hyaluronate". The inhibitory concentration IC$_{50}$ was 0.085 mM.

The inhibitory concentration IC$_{50}$ was also determined in a similar manner, except that the amount of chondroitin synthase aqueous solution (B-2) was changed from 1.5 U/mL to 45 U/mL. The inhibitory concentration IC$_{50}$ was 0.085 mM.

Example 10

Reaction solution (Z-10) was prepared by adding the following to 1 mL of aqueous solution T: 100 μL of 1 M monopotassium phosphoenolpyruvate aqueous solution, 10 μL of pyruvate kinase aqueous solution (D4-1-1) obtained in Preparation 4, and 10 of chondroitin synthase aqueous solution (B-2) obtained in Preparation 11; and was allowed to react at 30° C. for 2 hours. Sampling was performed during the reaction, and the uridine diphosphate concentration in the reaction solution was measured using HPLC (under the same conditions as in Example 1). Table 2 shows the results.

Further, after two hours of reaction, chondroitin was separated from the unreacted substrate by paper chromatography using filter paper, and then the origin was cut out and immersed in a liquid scintillation cocktail. The radioactive isotope was then measured using a liquid scintillation counter. The yield of chondroitin was calculated from the amount of uptake of labeled glucuronic acid. The yield of chondroitin was 5.0 mg.

Comparative Example 2

Chondroitin was synthesized in a similar manner as in Example 10, except that "pyruvate kinase aqueous solution (D4-1-1) obtained in Preparation 4" and "1 M monopotassium phosphoenolpyruvate aqueous solution" were not used, and the amount of chondroitin synthase aqueous solution (B-2) was changed from "10 μL" to "300 μL". The yield of chondroitin was 2.5 mg. The uridine diphosphate concentration in the reaction solution was measured in a similar manner as in Example 10. Table 2 shows the results.

Preparation 12

Cellulose synthase aqueous, solution (B-3) was obtained in a similar manner as in Preparation 1, except that a "gene encoding the amino acid sequence of SEQ ID NO: 12 derived from acetic acid bacteria" was used in place of the "gene encoding the amino acid sequence of SEQ ID NO: 1 derived from *Streptococcus equisimilis*".

<Measurement of the Specific Activity of Cellulose Synthase Aqueous Solution (B-3)>

Reaction solution (12) was prepared by adding 10 μL of cellulose synthase aqueous solution (B-3) obtained in Preparation 12 to 1 mL of aqueous solution U (50 mM phosphate buffer (pH of 7.0) containing 100 mM uridine diphosphate-β-glucose ($^{14}$C-labeled radioactive isotope-containing uridine diphosphate-β-glucose; radioactivity of 300 mCi/mmol), 100 mM sodium chloride, 10 mM magnesium chloride, and 5 mM oleic acid). Four such reaction solutions (12) were prepared and allowed to react at 30° C. for 5 minutes, 10 minutes, 15 minutes, and 20 minutes, respectively. Cellulose was separated from the unreacted substrate by paper chromatography using filter paper, and then the origin was cut out and immersed in a liquid scintillation cocktail. The radioactive isotope was then measured using a liquid scintillation counter. The yield of cellulose was calculated from the amount of uptake of $^{14}$C-labeled glucose.

The results were 1.3 mg after 5 minutes, 2.6 mg after 10 minutes, 3.7 mg after 15 minutes, and 5.1 mg after 20 minutes. The specific activity of cellulose synthase aqueous solution (B-3) was calculated from the relationship between the yield of cellulose and the reaction time. The result was 0.15 U/μL.

<Measurement of the Inhibitory Concentration $IC_{50}$ Against Cellulose Synthase>

The inhibitory concentration $IC_{50}$ was measured in a similar manner as in "Measurement of the inhibitory concentration $IC_{50}$ against hyaluronan synthase", except that "cellulose synthase aqueous solution (B-3) obtained in Preparation 12" was used in place of "hyaluronan synthase aqueous solution (B-1) obtained in Preparation 1", "substrate solution [1-3] (a solution obtained by dissolving uridine diphosphate-β-glucose to a concentration 20 mM in buffer solution B)" was used in place of "substrate solution [1-1]", and "cellulose derived from acetic acid bacteria (available from Tokyo Chemical Industry Co., Ltd.)" was used in place of "sodium hyaluronate". The inhibitory concentration $IC_{50}$ was 0.1 mM.

The inhibitory concentration $IC_{50}$ was also determined in a similar manner, except that the amount of cellulose synthase aqueous solution (B-3) was changed from 1.5 U/mL to 45 U/mL. The result was 0.1 mM.

Example 11

Reaction solution (Z-11) was prepared by adding the following to 1 mL of aqueous solution U: 10 μL of 1 M monopotassium phosphoenolpyruvate aqueous solution, 10 μL of pyruvate kinase aqueous solution (D4-1-1) obtained in Preparation 4, and 10 μL of cellulose synthase aqueous solution (B-3) obtained in Preparation 12; and was allowed to react at 30° C. for 2 hours. Sampling was performed during the reaction, and the uridine diphosphate concentration in the reaction solution was measured using HPLC (under the same conditions as in Example 1). Table 2 shows the results.

After two hours of reaction, cellulose was separated from the unreacted substrate by paper chromatography using filter paper, and then the origin was cut out and immersed in a liquid scintillation cocktail. The radioactive isotope was then measured using a liquid scintillation counter. The yield of cellulose was calculated from the amount of uptake of $^{14}C$-labeled glucose. The yield of cellulose was 10 mg.

Comparative Example 3

Cellulose was synthesized in a similar manner as in Example 11, except that "pyruvate kinase aqueous solution (D4-1-1) obtained in Preparation 4" and "1 M monopotassium phosphoenolpyruvate aqueous solution" were not used, and the amount of cellulose synthase aqueous solution (B-3) obtained in Preparation 12 was changed from "10 μL" to "300 μL". The yield of cellulose was 3.0 mg. The uridine diphosphate concentration in the reaction solution was measured in a similar manner as in Example 11. Table 2 shows the results.

Preparation 13

Starch synthase aqueous solution (B-4) was obtained in a similar manner as in Preparation 1, except that a "gene encoding the amino acid sequence of SEQ ID NO: 13 derived from *Saccharomyces cerevisiae*" was used in place of the "gene encoding the amino acid sequence of SEQ ID NO: 1 derived from *Streptococcus equisimilis*".

<Measurement of the Specific Activity of Starch Synthase Aqueous Solution (B-4)>

Reaction solution (13) was prepared by adding 10 μL of starch synthase aqueous solution (B-4) obtained in Preparation 13 to 1 mL of aqueous solution V (50 mM phosphate buffer (pH of 7.0) containing 100 mM uridine diphosphate-α-glucose ($^{14}C$-labeled radioactive isotope-containing uridine diphosphate-α-glucose; radioactivity of 300 mCi/mmol), 100 mM sodium chloride, 10 mM magnesium chloride, and 5 mM oleic acid). Four such solutions (13) were prepared and allowed to react at 30° C. for 5 minutes, 10 minutes, 15 minutes, and 20 minutes, respectively. Starch was separated from the unreacted substrate by paper chromatography using filter paper, and then the origin was cut out and immersed in a liquid scintillation cocktail. The radioactive isotope was then measured using a liquid scintillation counter. The yield of starch was calculated from the amount of uptake of $^{14}C$-labeled glucose. The results were 1.3 mg after 5 minutes, 2.5 mg after 10 minutes, 3.8 mg after 15 minutes, and 5.2 mg after 20 minutes. The specific activity of starch synthase aqueous solution (B-4) was calculated from the relationship between the yield of starch and the reaction time. The result was 0.15 U/μL.

<Measurement of the Inhibitory Concentration $IC_{50}$ Against Starch Synthase>

The inhibitory concentration $IC_{50}$ was measured in a similar manner as in "Measurement of the inhibitory concentration $IC_{50}$ against hyaluronan synthase (B-1)", except that "starch synthase aqueous solution (B-4) obtained in Preparation 13" was used in place of "hyaluronan synthase aqueous solution (B-1) obtained in Preparation 1", "substrate solution [1-4] (a solution obtained by dissolving uridine diphosphate-α-glucose to a concentration 20 mM in buffer solution B)" was used in place of "substrate solution [1-1]", and "starch (available from Wako Pure Chemical Industries, Ltd.)" was used in place of "sodium hyaluronate". The inhibitory concentration $IC_{50}$ was 0.2 mM.

The inhibitory concentration $IC_{50}$ was also determined in a similar manner, except that the amount of starch synthase aqueous solution (B-4) was changed from 1.5 U/mL to 75 U/mL. The result was 0.2 mM.

Example 12

Reaction solution (Z-12) was prepared by adding the following to 1 mL of aqueous solution V: 10 μL of 1 M monopotassium phosphoenolpyruvate aqueous solution, 10 μL of pyruvate kinase aqueous solution (D4-1-1) obtained in Preparation 4, and 10 μL of starch synthase aqueous solution (B-4) obtained in Preparation 13; and was allowed to react at 30° C. for 2 hours. Sampling was performed during the reaction, and the uridine diphosphate concentration in the reaction solution was measured using HPLC (under the same conditions as in Example 1). Table 2 shows the results.

Further, after two hours of reaction, starch was separated from the unreacted substrate by paper chromatography using filter paper, and then the origin was cut out and immersed in a liquid scintillation cocktail. The radioactive isotope was then measured using a liquid scintillation counter. The yield of starch was calculated from the amount of uptake of $^{14}C$-labeled glucose. The yield of starch was 9.0 mg.

Comparative Example 4

Starch was synthesized in a similar manner as in Example 12, except that "pyruvate kinase aqueous solution (D4-1-1) obtained in Preparation 4" and "1 M monopotassium phosphoenolpyruvate aqueous solution" were not used, and the amount of starch synthase aqueous solution (B-4) obtained in Preparation 13 was changed from "10 μL" to "500 μL". The yield of starch was 6.0 mg. The uridine diphosphate concentration in the reaction solution was measured in a similar manner as in Example 12. Table 2 shows the results.

TABLE 2

| | IC$_{50}$ (mM) against polysaccharide synthase (B) used | Concentration (mM) of ribonucleoside diphosphate in reaction solution | | | | | | Yield of polysaccharide (mg) |
|---|---|---|---|---|---|---|---|---|
| | | After 10 min | After 20 min | After 40 min | After 60 min | After 90 min | After 120 min | |
| Example 10 | 0.085 | 0.03 | 0.03 | 0.04 | 0.04 | 0.04 | 0.05 | 5.0 |
| Example 11 | 0.1 | 0.03 | 0.04 | 0.04 | 0.05 | 0.05 | 0.06 | 10 |
| Example 12 | 0.2 | 0.03 | 0.03 | 0.04 | 0.04 | 0.04 | 0.05 | 9.0 |
| Comparative Example 2 | 0.085 | 8 | 9 | 9 | 10 | 10 | 11 | 2.5 |
| Comparative Example 3 | 0.1 | 10 | 11 | 12 | 12 | 13 | 13 | 3.0 |
| Comparative Example 4 | 0.2 | 21 | 23 | 25 | 27 | 28 | 29 | 6.0 |

Examples 1 to 12 in which the concentration of ribonucleoside diphosphate was lower than 100 times the inhibitory concentration IC$_{50}$ showed a high yield of polysaccharide although the amount of polysaccharide synthase (B) used was small, compared to Comparative Examples 1 to 4. This indicates that Examples 1 to 12 had a very high yield of polysaccharide per unit enzyme. Moreover, the results show that, regardless of the type of polysaccharide synthase (B), a decrease in the concentration of ribonucleoside diphosphate results in an increase in the yield of polysaccharide per unit enzyme, thus enabling efficient polysaccharide production.

The results also show that allowing polysaccharide synthase (B) to act in the presence of ribonucleoside diphosphate conversion enzyme (D) results in a decrease in the concentration of ribonucleoside diphosphate, thus achieving a higher yield of polysaccharide.

INDUSTRIAL APPLICABILITY

The method for producing a polysaccharide of the present invention enables highly efficient polysaccharide production. The polysaccharide produced by the production method of the present invention can be used not only in cosmetic products, quasi drugs, medicinal products, and medical devices, but also in other products such as food.
Sequence Listings.txt

The invention claimed is:

1. A method for producing a hyaluronan, wherein steps (1) to (3) described below are simultaneously performed:

Step (1): producing a hyaluronan and a uridine diphosphate by allowing a hyaluronan synthase (B-1) to act on a uridine diphosphate-glucuronic acid and a uridine diphosphate-N-acetylglucosamine;

Step (2): producing a uridine triphosphate by allowing a uridine triphosphate synthase (D4-1) to act on the uridine diphosphate and a phosphate-containing compound (F); and Step (3): producing a uridine diphosphate-glucuronic acid by allowing a uridine triphosphate-monosaccharide-1-phosphate uridylyltransferase (G) to act on the uridine triphosphate and a 1-phospho-glucuronic acid, wherein initial concentrations of the uridine diphosphate-glucuronic acid and the uridine diphosphate-N-acetylglucosamine are 0.1 mM to 2M, initial concentration of hyaluronan synthase (B-1) is 0.1 to 100,000 U/L, wherein 1 U of hyaluronan synthase (B-1) represents the amount of enzyme to produce the hyaluronan and the uridine diphosphate from 1 μmol of the uridine diphosphate-glucuronic acid and the uridine diphosphate-N-acetylglucosamine per minute at 30° C. and pH of 7.0, wherein a duration in which the hyaluronan synthase (B-1) acts on the uridine diphosphate-glucuronic acid and the uridine diphosphate-N-acetylglucosamine is 10 minute or more, wherein in 10 to 100% of the duration, the concentration of the uridine diphosphate in the reaction solution is lower than 100 times an inhibitory concentration $IC_{50}$ against the hyaluronan synthase (B-1), and wherein the inhibitory concentration $IC_{50}$ refers to a concentration of the uridine diphosphate at which an enzyme activity of the hyaluronan synthase (B-1) is reduced by half under a condition where the hyaluronan synthase (B-1) has a concentration at which the hyaluronan synthase (B-1) acts on the uridine diphosphate-glucuronic acid and the uridine diphosphate-N-acetylglucosamine, wherein the uridine diphosphate-glucuronic acid and the uridine diphosphate-N-acetylglucosamine are used as a substrate and the uridine diphosphate is used as an inhibitor, and wherein the phosphate-containing compound (F) is at least one compound selected from the group consisting of triaminophosphine oxide, ω-phosphono-L-arginine, polyphosphoric acid, phosphoenolpyruvic acid and salts thereof, carbamoyl phosphate, 1,3-Bisphosphoglycerate, phosphocreatine, and nucleoside triphosphate.

2. The method for producing a hyaluronan according to claim 1, wherein an enzyme activity ratio $(Y_1)$ calculated from formula (1) is not lower than 0.1, $$\text{enzyme activity ratio } (Y_1) = V\max_1 / V\max_2 \qquad (1),$$

wherein $V\max_1$ is the enzyme activity of the uridine triphosphate synthase (D4-1) on the uridine diphosphate, and $V\max_2$ is the enzyme activity of the uridine triphosphate synthase (D4-1) on the uridine diphosphate-glucuronic acid and the uridine diphosphate-N-acetylglucosamine.

3. The method for producing a hyaluronan according to claim 1, wherein an enzyme activity ratio $(Y_2)$ calculated from formula (2) is not lower than 0.1, $$\text{enzyme activity ratio } (Y_2) = V\max_1 / V\max_3 \qquad (2),$$

where $V\max_1$ is the enzyme activity of the uridine triphosphate synthase (D4-1) on the uridine diphosphate, and $V\max_3$ is the enzyme activity of the hyaluronan synthase (B-1) on the uridine diphosphate-glucuronic acid and the uridine diphosphate-N-acetylglucosamine.

4. The method for producing a hyaluronan according to claim 1, wherein a Michaelis constant Km is lower than 100 times the inhibitory concentration $IC_{50}$, wherein the Michaelis constant Km refers to a Michaelis constant of reaction to synthesize the uridine triphosphate in the presence of the phosphate-containing compound (F), the using uridine diphosphate as a substrate and the uridine triphosphate synthase as an enzyme, and wherein the inhibitory concentration $IC_{50}$ refers to a concentration of the uridine diphosphate at which an enzyme activity of the hyaluronan synthase (B-1) is reduced by half under a condition where the hyaluronan synthase (B-1) has a concentration at which the hyaluronan synthase (B-1) acts on the uridine diphosphate-glucuronic acid and the uridine diphosphate-N-acetylglucosamine, wherein the uridine diphosphate-glucuronic acid and the uridine diphosphate-N-acetylglucosamine are used as substrates and the uridine diphosphate is used as an inhibitor.

* * * * *